US008196451B2

(12) United States Patent
Konno et al.

(10) Patent No.: US 8,196,451 B2
(45) Date of Patent: Jun. 12, 2012

(54) DETECTION SENSOR

(75) Inventors: Mitsuo Konno, Tsukuba (JP); Tsuyoshi Ikehara, Tsukuba (JP); Takayuki Takano, Tsukuba (JP); Takashi Mihara, Tokyo (JP)

(73) Assignees: National Institute of Advanced Industrial Science and Technology, Tokyo (JP); Olympus Corporation, Tokyo (JP)

( * ) Notice: Subject to any disclaimer, the term of this patent is extended or adjusted under 35 U.S.C. 154(b) by 221 days.

(21) Appl. No.: 12/661,194

(22) Filed: Mar. 12, 2010

(65) Prior Publication Data
US 2010/0223987 A1    Sep. 9, 2010

Related U.S. Application Data

(63) Continuation of application No. PCT/JP2008/067036, filed on Sep. 19, 2008.

(30) Foreign Application Priority Data

Sep. 28, 2007  (JP) ................................. 2007-255549

(51) Int. Cl.
*G01N 29/02* (2006.01)

(52) U.S. Cl. ..................... 73/24.06; 73/31.05; 73/61.49; 73/61.75; 73/61.79; 73/64.53

(58) Field of Classification Search ...... 73/24.01–24.06, 73/31.05–31.06, 54.41, 61.49, 61.75, 61.79, 73/64.53, 579
See application file for complete search history.

(56) References Cited

U.S. PATENT DOCUMENTS
7,681,433 B2 *  3/2010  Konno et al. ................ 73/24.06
2006/0273867 A1 *  12/2006  Piazza et al. ................. 333/189
2007/0052498 A1 *  3/2007  Pan et al. ..................... 333/186

FOREIGN PATENT DOCUMENTS
JP    2006-319387 A      11/2006
JP    2007-248324 A       9/2007
JP    2007248324 A  *    9/2007
WO    2007-148522 A1     12/2007

OTHER PUBLICATIONS

Nguyen, C T-C; Vibrating RF MEMS Technology: Fuel for an Integrated Micromechanical Circuit Revolution? The 13th International Conference on Solid-State Sensors, Actuators and Microsystems, Seoul, Korea; Jun. 5-9, 2005.

* cited by examiner

*Primary Examiner* — Hezron E Williams
*Assistant Examiner* — Rose M Miller
(74) *Attorney, Agent, or Firm* — Pearne & Gordon LLP

(57) ABSTRACT

There is provided a technique that can increase sensitivity of a resonator. A ratio Rb/Ra between an inner diameter Rb and an outer diameter Ra of the resonator 20 is appropriately selected, and thus there may be a fixed point where an r component (U(Ra) or U(Rb)) of displacement in a radial direction and an r component (V(Ra) or V(Rb)) of displacement in a tangential direction are 0 on an outer diameter portion or an inner diameter portion of the resonator 20. In this case, the resonator 20 is supported by a holding member 22 constituted by a single-span beam set so that a boundary condition on a side of the resonator 20 is pinned and a boundary condition on a side of an anchor that supports the resonator 20 is clamped at the fixed point, and this prevents vibration energy of the resonator 20 from being lost through the holding member 22, avoids a state to disturb a vibration mode, and achieves a sensor having high sensitivity.

6 Claims, 18 Drawing Sheets
(2 of 18 Drawing Sheet(s) Filed in Color)

U(Rb) ———
U(Ra) --------
V(Rb) —·—·—
V(Ra) ▬▬▬

FIG. 9A
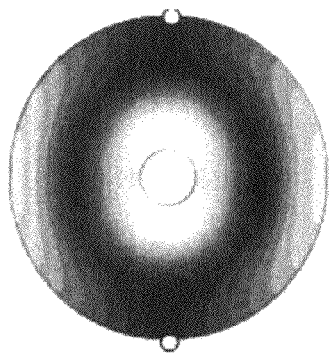
Rb/Ra=0.17
(1, 2) Mode
FIG. 9B
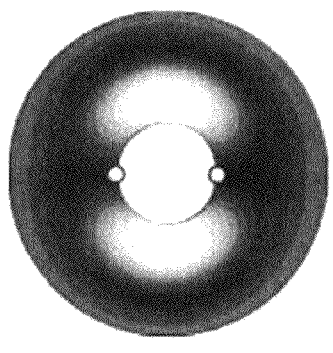
Rb/Ra=0.31
(1, 2) Mode
FIG. 9C
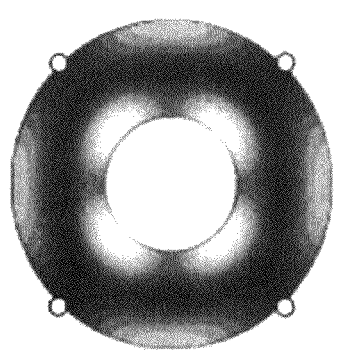
Rb/Ra=0.41
(2, 3) Mode
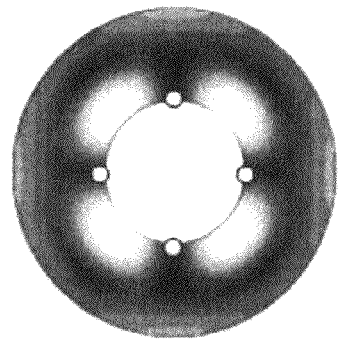
Rb/Ra=0.43
(2, 3) Mode
FIG. 9D
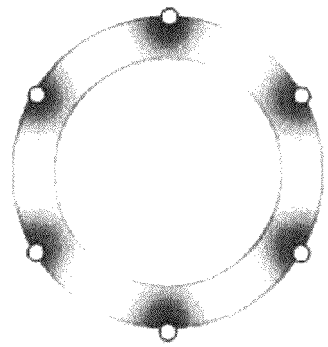
Rb/Ra=0.73
(3, 1) Mode
FIG. 9E

DETECTION SENSOR

BACKGROUND OF THE INVENTION

Field of the Invention

The present invention relates to a detection sensor suitable for use in detecting the presence of a substance having a mass, detecting the mass of the substance, or the like.

Development of micromachining techniques such as a micromachine/MEMS (Micro Electro Mechanical Systems) technique has allowed production of an extremely small mechanical resonator. This has allowed a reduction in mass of the resonator itself, and a resonator has been achieved having such high sensitivity that even a mass change due to adherence of an extremely minute substance (for example, molecule or virus) at a molecular level fluctuates s a frequency or an impedance characteristic. With such a resonator having high sensitivity, a sensor or the like that can detect the presence or an amount of an extremely minute substance can be configured.

A device that detects an amount of a substance by a frequency change or the like of a mechanical resonator is well-known as a QCM (Quarts Crystal Micro balance) sensor. This uses the nature that when a substance adheres to a crystal resonator, a vibration frequency fluctuates (lowers) depending on a mass of the adhering substance. The QCM sensor has superior performance as a mass sensor that measures a minute mass, and is further often used as a film thickness meter (vapor deposition monitor).

Since such a resonator has a significantly reduced size, thus has a higher frequency up to a GHz level, and can be made of Si, researches for integration into a semiconductor circuit have been developed.

High frequency filters often used in personal radio communication devices such as cell phones mainly include a dielectric resonator achieving a size reduction and higher performance of an electric resonator, a SAW filter using characteristics of acoustic waves, and a quarts crystal filter using mechanical vibration characteristics of a crystal resonator, and are widely used in high frequency portions in cell phones with the respective characteristics being taken advantage of. However, there is also a strong desire for lower costs together with a further size reduction and higher performance such as higher frequency of communication devices, and instead of the conventional filters, a new high frequency filter is desired that can be integrated into a semiconductor integrated circuit, that is, integrated into one chip to reduce a size and costs. A mechanical resonator produced by a MEMS machining technique is made of Si like a semiconductor, and is a possible choice thereof. Thus, basic researches for a higher frequency, a higher quality factor, or the like of a MEMS resonator, and researches on application of the MEMS resonator to a high frequency filter or a transmitter have been developed (for example, see Non-Patent Document 1).

One type of such a resonator is a disk-shaped resonator. Basic researches on mechanical vibration of the disk-shaped resonator have been long made, and it can be said that basic researches on vibration modes for specifying a vibration state of the disk-shaped resonator has been already finished.

Non-Patent Document 1: C. T.-C. Nguyen, "Vibrating RF MEMS Technology: Fuel for an Integrated Microchemical Circuit Revolution?." The 13th International Conference on Solid-State Sensors, Actuators and Microsystems (Transducers '05), Korea, Jun. 5-9, 2005

Researches for MEMS disk-shaped resonators include an increase in quality factor for higher sensitivity, driving and detection methods of resonators, characteristic control by a combination of resonators for application to filters, or the like, and continuous researches thereon have been diligently performed.

SUMMARY OF THE INVENTION

A detection sensor according to the present invention comprises: a disk-shaped resonator; a driving unit that drives the resonator; and a detection unit that detects a change in vibration of the resonator to detect a substance. Such a detection sensor detects a change in vibration of the resonator caused by an influence of a mass of the substance, and thus detects the substance. For the detection of the substance, not only the presence of the substance but also an amount of the substance may be detected.

Such a resonator vibrates in a particular resonant mode. Thus, since there are a region with large amplitude and a region with substantially no vibration in a surface of the resonator, and the regions differ depending on resonant modes, detection sensitivity differs depending on where the substance to be detected adheres on the surface of the resonator. Thus, the inventors considered that even if the substance uniformly adheres or is adsorbed to the surface of the resonator, there are variations in sensitivity depending on regions, and thus sensitivity can be increased in this respect.

One means for increasing sensitivity of such a resonator is to cause a substance to adhere or be adsorbed to a region with high sensitivity (large amplitude) in a focused and selective manner. This has been already proposed by the applicant (Japanese Patent Laid-Open No. 2007-187485).

Also, a method in which using a characteristic that a resonator has different amplitudes depending on regions, the resonator is supported at a region with a few vibrations to reduce loss caused by prevention of vibration of the resonator and increase sensitivity has been also proposed by the applicant (Japanese Patent Application No. 2006-73742).

An outline of the latter proposal will be now described.

A quality factor that is a parameter for evaluating a resonator is determined by whether the resonator does not lose vibration energy, and can be expressed by a relationship in Expression (1).

[Expression 1]

$$\frac{1}{Q_{total}} = \frac{1}{Q_{air}} + \frac{1}{Q_{TED}} + \frac{1}{Q_{anchorLoss}} + \frac{1}{Q_{others}} \quad (1)$$

Specifically, main causes for loss of the vibration energy of the resonator include:
1) loss $Q_{air}$ due to an ambient medium such as air;
2) loss $Q_{TED}$ due to vibration and deformation of the resonator;
3) loss $Q_{anchor\,Loss}$ due to a holding member of the resonator; and other losses $Q_{others}$.

To reduce energy loss to the ambient medium typified by air that determines $Q_{air}$ in 1), the vibration of the resonator is controlled to select a vibration mode with high vibration energy of the resonator but low energy transfer to the ambient medium. For example, a disk-shaped mechanical resonator vibrates only in the in-disk-face direction of the resonator (in a cylindrical coordinate, vibration only in r and θ directions without vibration in a Z direction), and the resonator rarely vibrates like a drum head (in the Z direction) to transfer high vibration energy to an ambient medium.

For $Q_{TED}$ in 2), the resonator vibrates and is deformed, and the deformation causes adiabatic expansion or adiabatic compression. Thus, an adiabatic expansion region is cooled, while an adiabatic compression region is heated, a temperature gradient occurs in the resonator, and the temperature is transferred and averaged and thus energy is lost. Specifically, it can be said that this energy loss is determined by a vibration mode and a material of the resonator.

$Q_{anchor\ Loss}$ in 3) is a loss due to the holding portion of the resonator, and caused by the vibration of the resonator being transferred to the holding portion. For example, it is supposed that energy loss can be eliminated by providing the holding portion at a region without the vibration of the resonator, but for a general disk-shaped resonator, such a condition has not been found as long as Si single crystal that is the most general resonator material is used.

For example, a wine-glass mode (2, 1) is the best known resonant mode of a disk-shaped resonator. Displacement U (r, θ) in a radial direction and displacement V (r, θ) in a tangential direction as a mode function in the vibration of such a disk-shaped resonator can be expressed by the following Expression (2):

[Expression 2]

$$U(r, \theta) = \left[ A \frac{\partial}{\partial r} J_n(hr) + B \frac{n}{r} J_n(kr) \right] \cos n\theta \quad (2)$$

$$V(r, \theta) = -\left[ A \frac{n}{r} J_n(hr) + B \frac{\partial}{\partial r} J_n(kr) \right] \sin n\theta$$

The wine-glass mode (2, 1) is a resonant mode with the lowest frequency, and for a state of the vibration in the (2, 1) mode, as expressed by Expression (2), an r component has a finite value at all r except r=0 of the resonator in a radial direction, which changes in a circumferential direction according to cos 2θ, and vibration in the radial direction is eliminated at angles of θ=π/4, 3π/4, −3π/4 and −π/4. Such a position is referred to as a nodal point, and a method of holding the resonator at the position is also proposed.

However, the (2, 1) mode is a compound mode and also has a vibration component in the tangential direction, thus the r component has a finite value at all r except r=0 also in vibration in the tangential direction, which changes in the circumferential direction according to sin 2θ. Thus, sin 2θ is 1, −1, 1, −1 on V(r, θ) at the angles of θ=π/4, 3π/4, −3π/4 and −π/4 where U(r, θ) is 0, that is, cos 2θ is 0, and the amplitude becomes maximum to the contrary. Specifically, the circular resonator that vibrates in the wine-glass mode (2, 1) does not have a region where vibrations of both a radial component and a tangential component are 0.

However, the inventors have diligently studied and found a method for providing a resonator having a region where vibrations of both a radial component and a tangential component are 0 unlike the above-described example.

In the method thus found, the resonator has a ring shape with an opening at the center, and an outer diameter thereof is Ra and an inner diameter thereof is Rb. For displacement in a position r on a position coordinate (r, θ) when this resonator vibrates, displacement in a radial direction is indicated by U(r) and displacement in a tangential direction is indicated by V(r) as expressed in Expression (3), and thus the outer diameter Ra and the inner diameter Rb that substantially satisfy U(r)=0 or V(r)=0 when r=Ra or Rb form the resonator.

[Expression 3]

$$U(r) = \frac{\partial}{\partial r} J_n(hr) + A_6 \frac{n}{r} J_n(kr) + A_7 \frac{\partial}{\partial r} Y_n(hr) + A_8 \frac{n}{r} Y_n(kr) \quad (3)$$

$$V(r) = \frac{n}{r} J_n(hr) + A_6 \frac{\partial}{\partial r} J_n(kr) + A_7 \frac{n}{r} Y_n(hr) + A_8 \frac{\partial}{\partial r} Y_n(kr)$$

where $$h = \omega \sqrt{\frac{\rho(1-\sigma^2)}{E}}, \quad k = \omega \sqrt{\frac{\rho(2+2\sigma)}{E}}, \quad k = h \sqrt{\frac{2}{1-\sigma}}$$

σ: Poisson's ratio of resonator material, E: Young's modulus of resonator material, ρ: density of resonator material, ω: angular frequency, A6, A7 and A8: coefficient, n: degree of vibration mode In Expression (3), A6, A7 and A8 are constants uniquely determined by a natural vibration mode specified by the outer diameter Ra and the inner diameter Rb of the resonator, the Young's modulus, the density and the Poisson's ratio of the resonator material, and a boundary condition (in this case, a free-free condition) of the resonator. Specifically, when A5=1 in Expression (9) described later, A6, A7 and A8 are solutions to simultaneous linear equations in Expression (9).

As such, in the ring-shaped resonator, there may appear a region without vibration in the outer diameter portion or the inner diameter portion depending on a ratio between the outer diameter Ra and the inner diameter Rb. The ratio at this time differs depending on a Poisson's ratio of a material of the resonator, a mode number n of a vibration mode in vibration of the resonator, and a degree m of harmonic vibration.

In the case where U(r)=0 or V(r)=0 is substantially satisfied when r=Ra in Expression (3), the resonator has a region without vibration in the outer diameter portion. In the case where U(r)=0 or V(r)=0 is substantially satisfied when r=Rb in Expression (3), the resonator has a region without vibration in the inner diameter portion.

Further, in the case where U(r)=0 is substantially satisfied when r=Ra or Rb in Expression (3), the resonator has a region without vibration in a position θ where sin(nθ)=0. Also, in the case where V(r)=0 is substantially satisfied when r=Ra or Rb in Expression (3), the resonator has a region without vibration in a position θ where cos(nθ)=0.

As such, when the resonator has a region where vibrations of both the radial component and the tangential component can be eliminated, the resonator can be supported at the region to increase sensitivity.

The present invention allows not only the case where the condition of U(r)=0 or V(r)=0 is completely satisfied but the case where the condition is substantially satisfied. This is because forming a resonator having an outer diameter Ra and an inner diameter Rb that can completely satisfy the condition of U(r)=0 or V(r)=0 is difficult because of production errors or the like, and also there is a case where vibration is sufficiently low in an outer diameter portion or an inner diameter portion even in the case of being slightly beyond the condition of U(r)=0 or V(r)=0.

Since the region that satisfies the above-described condition can eliminate vibrations of both the radial component and the tangential component of the resonator, the resonator is preferably held at the region (hereinafter, such a regions is referred to as a "fixed point").

The inventors have further continued studying and found the problems described below.

Specifically, the inventors performed an analysis with conditions of specific details being set, and found that displacement occurs near a support portion that supports the resonator even if the resonator is supported at the fixed point that satisfies the above-described condition.

The fixed point that satisfies the above-described condition is literally a "point". If this fixed point can be purely held as a point, there is no possibility that vibration energy of the resonator is lost through a holding member or that mounting the holding member exerts an influence on a vibration mode to change a vibration frequency. However, the fixed point is generally a point, while an actual holding member needs a limited size. Thus, if the resonator is held without any measures, vibration energy of the resonator is lost through the holding member to disturb the vibration mode. The inventors understood that this causes the displacement near the support portion as described above.

The present invention then achieved comprises: a disk-shaped resonator having a vibration characteristic changed by adherence or adsorption of a substance having a mass; a driving unit that causes vibration of the resonator; and a detection unit that detects a change in vibration of the resonator to detect the substance. The resonator has a ring shape with an outer diameter Ra and an inner diameter Rb with an opening formed at the center, and the resonator is formed of the outer diameter Ra and the inner diameter Rb that substantially satisfy $U(r)=0$ or $V(r)=0$ when $r=Ra$ or $Rb$ for displacement $U(r)$ in a radial direction and displacement $V(r)$ in a tangential direction expressed by Expression (3) in a position r on a position coordinate (r, θ) when the resonator vibrates. Further, the resonator is supported on an anchor by a single-span beam set so that a boundary condition on a side of the resonator is pinned and a boundary condition on a side of the anchor that supports the resonator is clamped.

The single-span beam preferably has a length and a width set so that a vibration frequency thereof is substantially equal to a vibration frequency of the resonator.

The detection unit can detect an amount of substance adhering to the resonator.

For adherence or adsorption of the substance, for example, an adsorption material that can efficiently adsorb molecules may be added to a surface of the resonator. This includes a global recognition material and a selective recognition material. The global recognition material is a polymer that does not have high selectivity but adsorbs particular molecule groups, for example, alcohol or ether. The polymer may be fabricated into nano-fiber or made porous to increase a surface area. The recognition material having high selectivity includes a biological material that causes an antigen-antibody reaction, a combination of an acceptor and a receptor, a probe having a particular base sequence hybridized with genes, DNA or RNA. A lipid bilayer membrane may be used.

For such a detection sensor, the substance to be detected may be a particular molecule, or multiple types of molecules having a particular property or characteristic. Thus, the detection sensor can be used as, for example, a gas detection sensor or an odor sensor. A particular type of molecule only is desirably detected with high selectivity when gas or biological molecules, airborne molecules in a living space, volatile molecules, or the like are detected as a particular molecule. Also, a plurality of detection sensors having such high selectivity may be used to recognize multiple types of molecules or extend an application range of use. A molecule group having a particular characteristic or a molecule group having the same side chain may be detected, which is referred to as global recognition. In this case, a plurality of detection sensors may be used to recognize a molecule group from a difference in detectability between the plurality of detection sensors by signal processing or processing with software.

Also, the configuration may be changed to operate in a liquid to detect a particular protein, enzyme, sugar chain, or the like.

Detection of a minute mass can be used for a film thickness monitor in thin film forming, or biotechnological researches such as an antigen-antibody reaction or a protein adsorption action. The detection sensor of the present invention is suitable for such uses.

Also, it may be conceivable that the detection sensor or the resonator of the present invention is used for a small and stable gas sensor with high sensitivity for domestic or personal use, or a portable and disposable sensor for detecting harmful substances suspended in air or the like. The application range is further extended with increasing sensitivity, and the sensor can be developed to detect and identify odors. Further, uses other than the above do not prevent use of the detection sensor of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows a relationship between a ratio between an outer diameter and an inner diameter of the disk-shaped resonator and values of U(Ra), U(Rb), V(Ra) and V(Rb) in an n=1 mode.

FIG. 3 shows a relationship between a ratio between the outer diameter and the inner diameter of the disk-shaped resonator and values of U(Ra), U(Rb), V(Ra) and V(Rb) in an n=2 mode.

FIG. 4 shows a relationship between a ratio between the outer diameter and the inner diameter of the disk-shaped resonator and values of U(Ra), U(Rb), V(Ra) and V(Rb) in an n=3 mode.

FIG. 5 shows a relationship between a ratio between the outer diameter and the inner diameter of the disk-shaped resonator and a Poisson's ratio when Expression (12) is satisfied in the n=1 mode.

FIG. 6 shows a relationship between a ratio between the outer diameter and the inner diameter of the disk-shaped resonator and a Poisson's ratio when Expression (12) is satisfied in the n=2 mode.

FIG. 7 shows a relationship between a ratio between the outer diameter and the inner diameter of the disk-shaped resonator and a Poisson's ratio when Expression (12) is satisfied in the n=3 mode.

mode.

FIG. 9 shows representative examples of a resonator having a fixed point on an outer periphery or an inner periphery;

DESCRIPTION OF SYMBOLS

10 . . . sensor (detection sensor), 20 . . . resonator, 21 . . . opening, 22 . . . support member, 40 . . . detection unit

DESCRIPTION OF PREFERRED EMBODIMENTS

Now, the present invention will be described in detail based on an embodiment shown in the accompanying drawings.

Figure 1A:
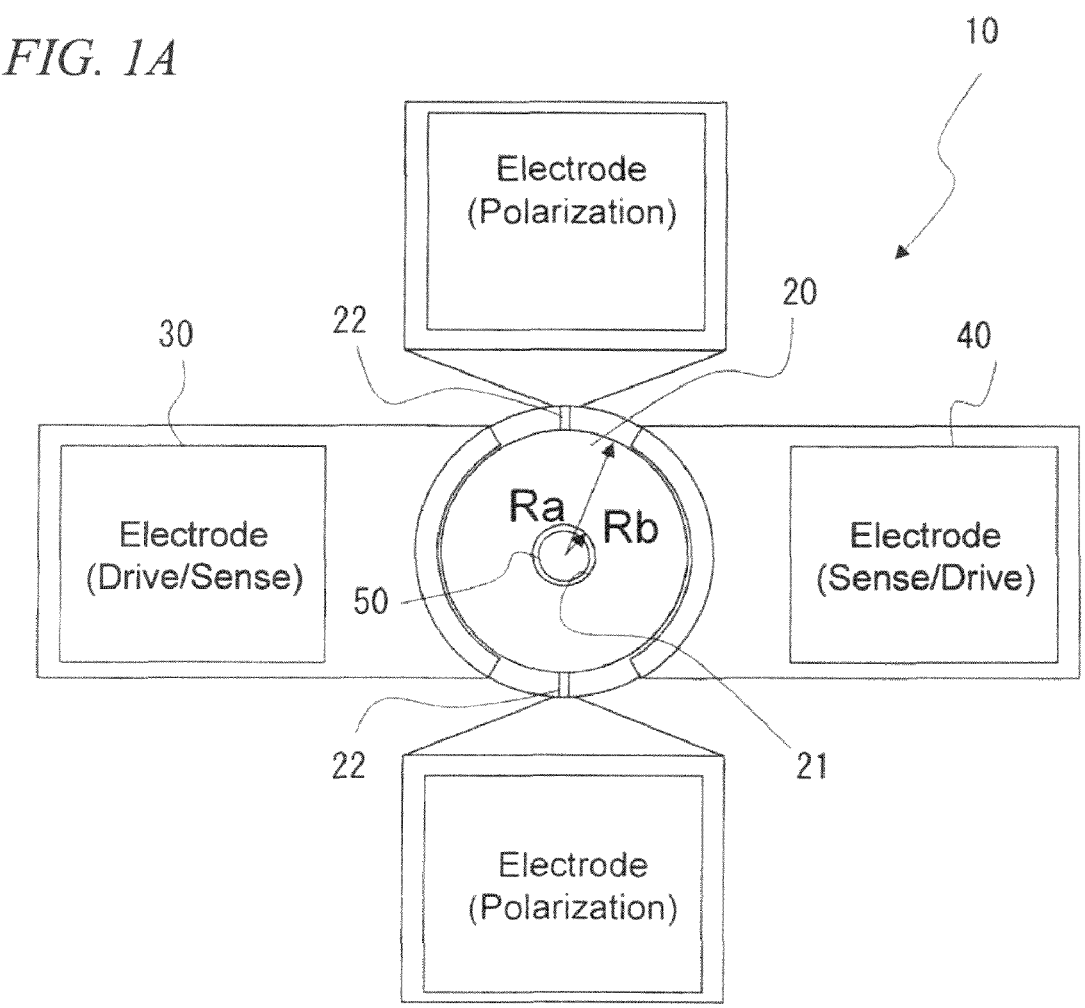
FIG. 1A shows a configuration of a sensor of an embodiment.
Figure 1B:
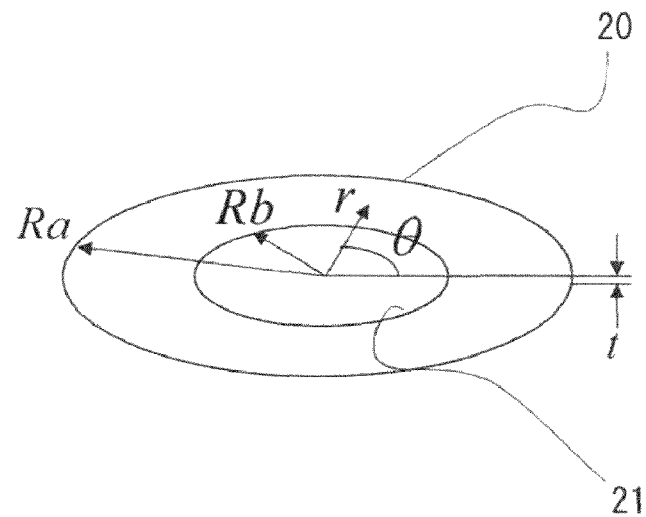
FIG. 1B is a perspective view of a disk-shaped resonator.

FIG. 1 illustrates a basic configuration of a sensor (detection sensor) 10 of the embodiment.

The sensor 10 shown in FIG. 1 has a disk shape and generally has a circular, rectangular, or other appropriate shape, and comprises a resonator 20 having a vibration frequency changed when an object to be detected such as a molecule having a mass adheres to the resonator 20; a drive source 30 for causing vibration of the disk-shaped resonator 20; and a detection unit 40 that detects a change in vibration characteristic of the resonator 20.

The drive source 30 uses an electrostatic effect or a piezoelectric effect by a current generated from an unshown external controller to cause vibration of the resonator 20.

The detection unit 40 detects the vibration of the resonator 20 also by the electrostatic effect or the piezoelectric effect to output as an electric signal. If a substance having a mass adheres to the resonator 20 at this time, the number of vibrations of the resonator 20 is changed by the influence of the mass. For the detection unit 40, electrical vibration output from the detection unit 40 can be monitored to detect the presence of adherence of the substance to the resonator 20 or an amount of adherence of the substance to the resonator 20.

In such a sensor 10, the resonator 20 has an opening 21 formed at the center. The resonator 20 is supported only by a support member 22 connected to a predetermined position on an outer peripheral portion, and the remaining portions are all in a free state.

When an outer diameter of the resonator 20 is Ra and a diameter of the opening 21 is Rb, the outer diameter Ra of the resonator 20 and the diameter of the opening 21 (an inner diameter of the resonator 20) Rb are preferably set so that Rb/Ra substantially satisfies the following condition.

Vibrations that occur in the disk-shaped resonator 20 include three modes: (a) a radial mode (mode with vibration only in a radial direction (r direction)), (b) a tangential mode (mode with vibration only in a θ direction), and (c) a compound mode (mode with a combination of vibration in the radial direction and vibration in the θ direction).

A determination expression of a resonance frequency in the compound mode of the resonator 20 is as expressed by the following Expression (4).

[Expression 4]

$$f(K) = \begin{vmatrix} a_{11} & a_{12} & a_{13} & a_{14} \\ a_{21} & a_{22} & a_{23} & a_{24} \\ a_{31} & a_{32} & a_{33} & a_{34} \\ a_{41} & a_{42} & a_{43} & a_{44} \end{vmatrix} = 0 \quad (4)$$

where $a_{11}$ to $a_{44}$ are as described below.

[Expression 5]

$$a_{11} = -J_n(K)[(K\xi)^2/2 - n(n+1) + M_n(K)], \quad (5)$$
$$a_{12} = nJ_n(K\xi)[M_n(K\xi) - (n+1)]$$
$$a_{13} = -Y_n(K)[(K\xi)^2/2 - n(n+1) + N_n(K)],$$
$$a_{14} = nY_n(K\xi)[N_n(K\xi) - (n+1)]$$
$$a_{21} = -J_n(L)[(L\xi)^2/2 - n(n+1) + M_n(L)],$$
$$a_{22} = nJ_n(L\xi)[M_n(L\xi) - (n+1)]$$
$$a_{23} = -Y_n(L)[(L\xi)^2/2 - n(n+1) + N_n(L)],$$
$$a_{24} = nY_n(L\xi)[N_n(L\xi) - (n+1)]$$
$$a_{31} = -nJ_n(K)[M_n(K) - (n+1)],$$
$$a_{32} = J_n(K\xi)[(K\xi)^2/2 - n(n+1) + M_n(K\xi)]$$
$$a_{33} = -nY_n(K)[N_n(K) - (n+1)],$$
$$a_{34} = Y_n(K\xi)[(K\xi)^2/2 - n(n+1) + N_n(K\xi)]$$
$$a_{41} = -nJ_n(L)[M_n(L) - (n+1)],$$
$$a_{42} = J_n(L\xi)[(L\xi)^2/2 - n(n+1) + M_n(L\xi)]$$
$$a_{43} = -nY_n(L)[N_n(L) - (n+1)],$$
$$a_{44} = Y_n(L\xi)[(L\xi)^2/2 - n(n+1) + N_n(L\xi)]$$
where
$$K = hR_a, \, L = hR_b, \, M_n(x) = xJ_{n-1}(x)/J_n(x),$$
$$N_n(x) = xY_{n-1}(x)/Y_n(x)$$
$$\xi = \sqrt{2/(1-\sigma)}, \quad h = \omega\sqrt{\rho(1-\sigma^2)/E}$$

where σ: Poisson's ratio of resonator material, E: Young's modulus of resonator material, ρ: density of resonator material, and ω: angular frequency (=2πf).

Two boundaries, that is, the outer diameter portion and the inner diameter portion in the resonator 20 having the opening 21 are under a free-free condition, and thus it is found that residual stress in a radial direction and residual stress in a tangential direction are eliminated to determine four boundary conditions. Also, displacement U(r, θ) in the radial direction and displacement V(r, θ) in the tangential direction as a mode function can be expressed by the following expression.

[Expression 6]

$$U(r,\theta) = \left[ \begin{array}{c} A_5 \dfrac{\partial}{\partial r} J_n(hr) + A_6 \dfrac{n}{r} J_n(kr) + A_7 \dfrac{\partial}{\partial r} Y_n(hr) + \\ A_8 \dfrac{n}{r} Y_n(kr) \end{array} \right] \cos n\theta \quad (6)$$

$$V(r,\theta) = \left[ \begin{array}{c} A_5 \dfrac{n}{r} J_n(hr) + A_6 \dfrac{\partial}{\partial r} J_n(kr) + A_7 \dfrac{n}{r} Y_n(hr) + \\ A_8 \dfrac{\partial}{\partial r} Y_n(kr) \end{array} \right] \sin n\theta$$

where $$h = \omega\sqrt{\dfrac{\rho(1-\sigma^2)}{E}},\ k = \omega\sqrt{\dfrac{\rho(2+2\sigma)}{E}},\ k = h\sqrt{\dfrac{2}{1-\sigma}}$$

The four boundary conditions described above can be applied to the Expression (6) to calculate the following relational expression.

[Expression 7]

$$\begin{bmatrix} a_{11} & a_{12} & a_{13} & a_{14} \\ a_{21} & a_{22} & a_{23} & a_{24} \\ a_{31} & a_{32} & a_{33} & a_{34} \\ a_{41} & a_{42} & a_{43} & a_{44} \end{bmatrix} \begin{bmatrix} A_5 \\ A_6 \\ A_7 \\ A_8 \end{bmatrix} = 0 \quad (7)$$

Further, the determination expression of the resonance frequency in Expression (3) means that Expression (7) is satisfied at any A5, A6, A7 and A8, and the condition therefor is the determinant=0 in the 4×4 matrix in Expression (7). This is Expression (3) that determines the resonance frequency.

The coefficients A5, A6, A7 and A8 in Expression (6) as a mode function have not yet been determined, and a vibration state of the resonator 20 is not determined until these coefficients are determined. Also, since Expression (7) is satisfied at any A5, A6, A7 and A8 under the resonant condition, the coefficients A5, A6, A7 and A8 in resonance have not been determined and cannot be determined as they are. However, the matrix in Expression (7) is divided into primary expressions to provide the following Expression (8).

[Expression 8]

$$a_{11}A_5 + a_{12}A_6 + a_{13}A_7 + a_{14}A_8 = 0$$

$$a_{21}A_5 + a_{22}A_6 + a_{23}A_7 + a_{24}A_8 = 0$$

$$a_{31}A_5 + a_{32}A_6 + a_{33}A_7 + a_{34}A_8 = 0$$

$$a_{41}A_5 + a_{42}A_6 + a_{43}A_7 + a_{44}A_8 = 0 \quad (8)$$

Among the four primary expressions in Expression (8) thus calculated, arbitrary three expressions are chosen, and a coefficient can be determined as a ratio to any one of the coefficients A5, A6, A7 and A8 therein. For example, the upper three expressions are chosen from Expression (8) and all divided by A5, and then simultaneous linear equations can be obtained as in the following Expression (9).

[Expression 9]

$$a_{11} + a_{12}\dfrac{A_6}{A_5} + a_{13}\dfrac{A_7}{A_5} + a_{14}\dfrac{A_8}{A_5} = 0 \quad (9)$$

$$a_{21} + a_{22}\dfrac{A_6}{A_5} + a_{23}\dfrac{A_7}{A_5} + a_{24}\dfrac{A_8}{A_5} = 0$$

$$a_{31} + a_{32}\dfrac{A_6}{A_5} + a_{33}\dfrac{A_7}{A_5} + a_{34}\dfrac{A_8}{A_5} = 0$$

From this Expression (9), coefficient ratios A6/A5, A7/A5 and A8/A5 with A5 as the denominator can be calculated. This result is assigned to Expression (6), and thus the displacement in the radial direction and the displacement in the tangential direction in resonance, that is, the mode function can be all determined. The upper three expressions in Expression (8) are herein used, but arbitrary different three expressions may be used for calculation. Four different simultaneous linear equations are herein obtained, but all the calculated results are the same.

All the results are proportional to A5, and thus there is no essential change in the mode function with A5=1. Thus, an r component in the radial direction in each mode is indicated as U(r) and an r component in the tangential direction is indicated as V(r) in each mode again with A5=1, and then the mode function in Expression (6) is expressed as in the following Expression (10).

[Expression 10]

$$U(r,\theta) = U(r)\cos n\theta$$

$$V(r,\theta) = V(r)\sin n\theta \quad (10)$$

U(r) and V(r) are as in the following Expression (11).

[Expression 11]

$$U(r) = \dfrac{\partial}{\partial r} J_n(hr) + A_6 \dfrac{n}{r} J_n(kr) + A_7 \dfrac{\partial}{\partial r} Y_n(hr) + A_8 \dfrac{n}{r} Y_n(kr) \quad (11)$$

$$V(r) = \dfrac{n}{r} J_n(hr) + A_6 \dfrac{\partial}{\partial r} J_n(kr) + A_7 \dfrac{n}{r} Y_n(hr) + A_8 \dfrac{\partial}{\partial r} Y_n(kr)$$

The analysis is made for the circular disk-shaped resonator 20 having the opening 21 unlike a general disk-shaped resonator. In the resonator 20, U(r) and V(r) in Expression (11) significantly change depending on the ratio between the outer diameter Ra and the inner diameter Rb of the resonator 20, and U(r) or V(r) may be 0 when the ratio between the outer diameter Ra and the inner diameter Rb of the resonator 20 becomes a particular value.

For example, when U(Ra)=0 on the outer diameter Ra of the resonator 20, vibration in the outer diameter portion of the resonator 20 is eliminated. Thus, the resonator 20 is supported by the support member 22 at the outer diameter potion. Even if V(Ra)≠0 at this time, the displacement in the tangential direction is V(Ra) multiplied by sin(nθ) as shown in Expression (10), and vibration does not occur at V(r, θ) in Expression (10) at the position where sin(nθ)=0. In the vibration mode of n=1, the resonator 20 is held by the support member 22 at positions of V(Ra, 0) and V(Ra, π), thereby preventing vibration energy of the resonator 20 from being lost through the support member 22.

On the other hand, in the case where V(Ra)=0, even if U(Ra)≠0, the displacement in the radial direction is U(Ra) multiplied by cos(nθ), and thus the resonator 20 may be held at a position where cos(nθ)=0.

The holding method at the outer diameter portion of the disk-shaped resonator 20 with the opening is herein described, but for holding at the inner diameter portion, the position can be determined by the same concept.

FIGS. 2 to 4 show states of changes of an r component in each of the vibration modes from n=1 to n=3, that is, U(r) and V(r) in Expression (11), with the ratio Rb/Ra between the inner diameter Rb and the outer diameter Ra on the abscissa. In this case, the resonator 20 is supposed to be made of Si single crystal, and a Poisson's ratio is σ=0.28. n is a mode number of the vibration mode, and m is a degree of harmonic vibration.

FIGS. 2 to 4 show the lowest resonance frequency (m=1) to the fourth resonance frequency (m=4) in each mode, and indicate this as (n, m) according to a general mode expression.

Figure 2A:
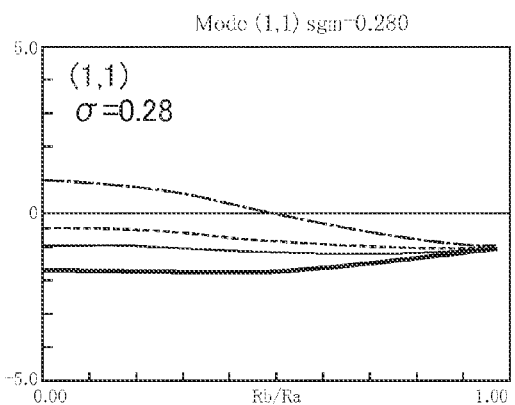
FIG. 2A is a relationship diagram in a (1, 1) mode.
Figure 2B:
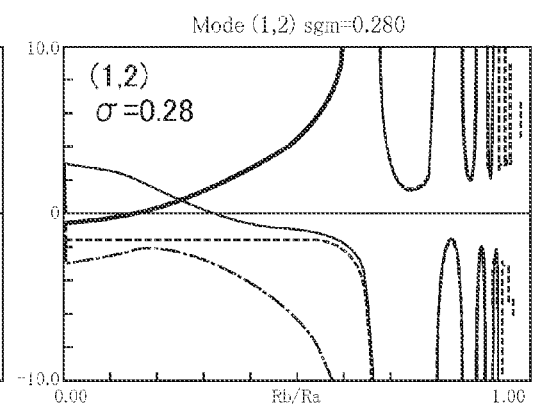
FIG. 2B is a relationship diagram in a (1, 2) mode.
Figure 2C:
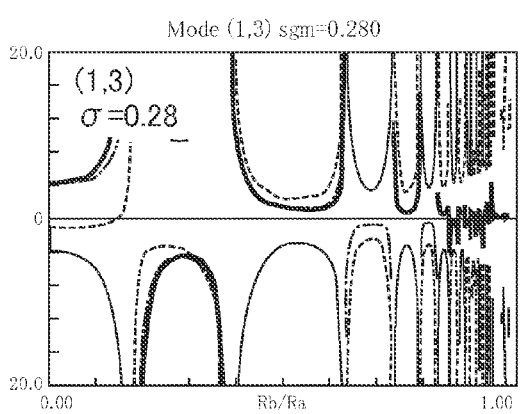
FIG. 2C is a relationship diagram in a (1, 3) mode.
Figure 2D:
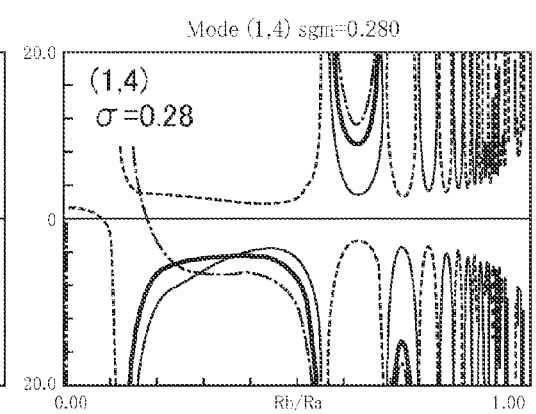
FIG. 2D is a relationship diagram in a (1, 4) mode.
Figure 3A:
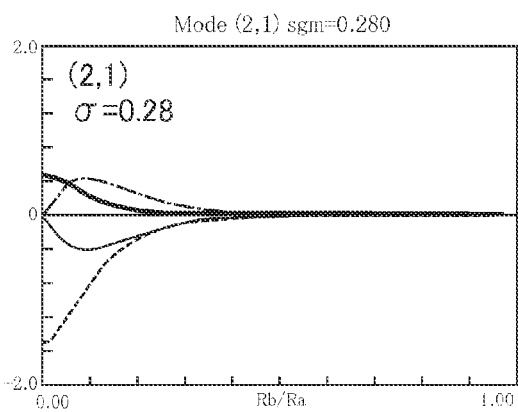
FIG. 3A is a relationship diagram in a (2, 1) mode.
Figure 3B:
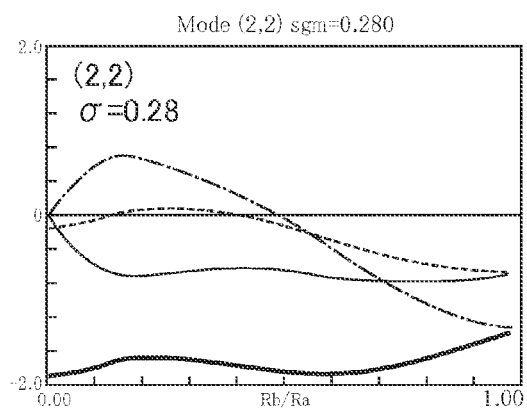
FIG. 3B is a relationship diagram in a (2, 2) mode.
Figure 3C:
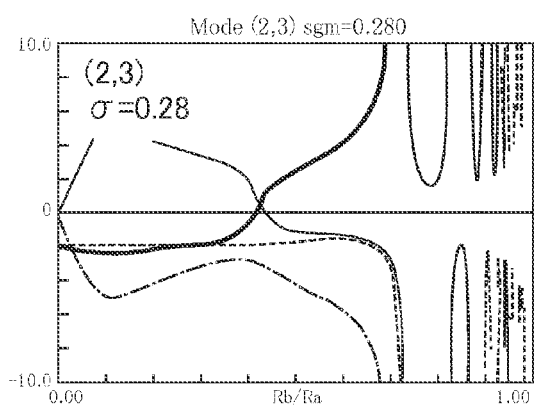
FIG. 3C is a relationship diagram in a (2, 3) mode.
Figure 3D:
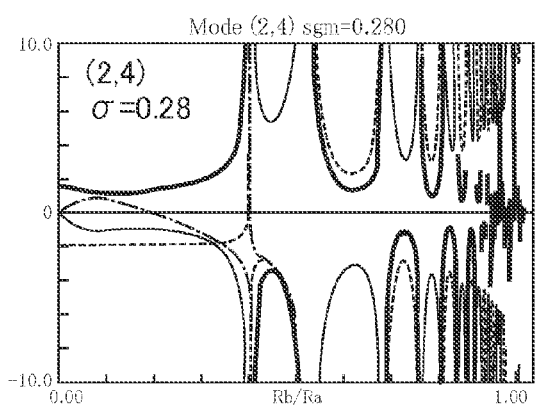
FIG. 3D is a relationship diagram in a (2, 4) mode.
Figure 4A:
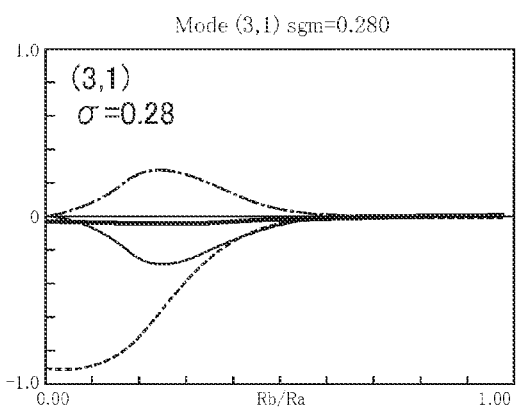
FIG. 4A is a relationship diagram in a (3, 1) mode.
Figure 4B:
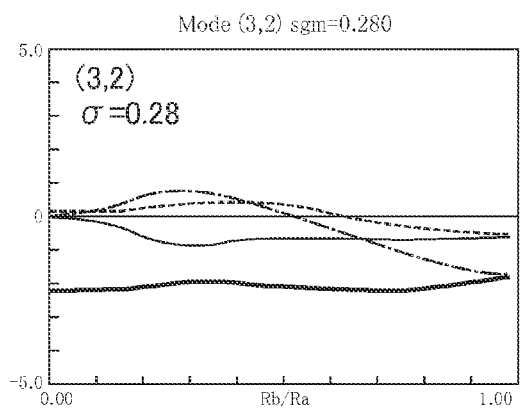
FIG. 4B is a relationship diagram in a (3, 2) mode.
Figure 4C:
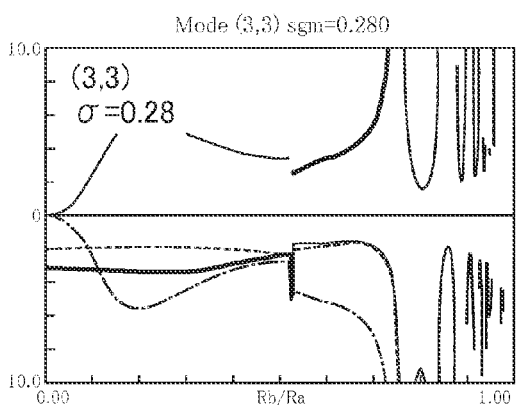
FIG. 4C is a relationship diagram in a (3, 3) mode.
Figure 4D:
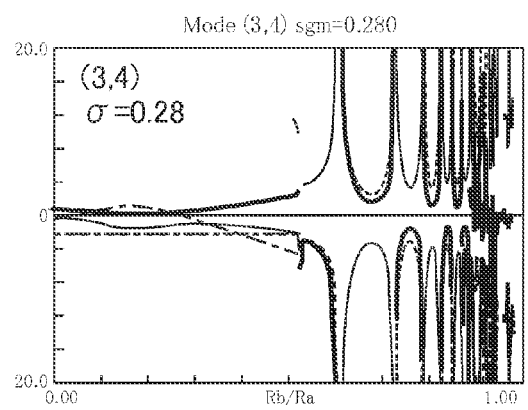
FIG. 4D is a relationship diagram in a (3, 4) mode.
Figure 5A:
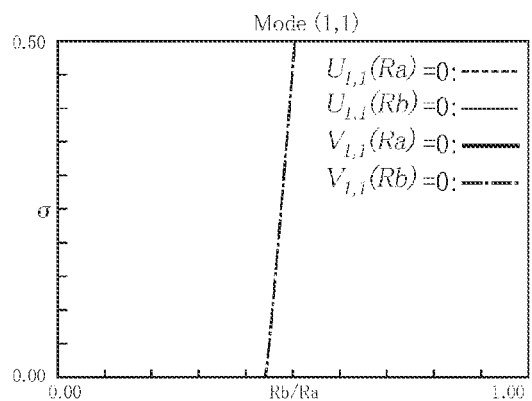
FIG. 5A is a relationship diagram in the (1, 1) mode.
Figure 5B:
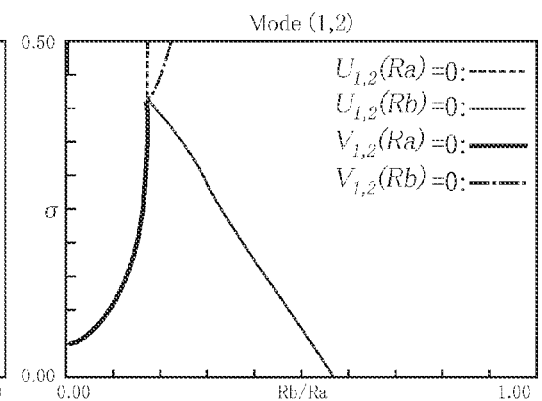
FIG. 5B is a relationship diagram in the (1, 2) mode.
Figure 5C:
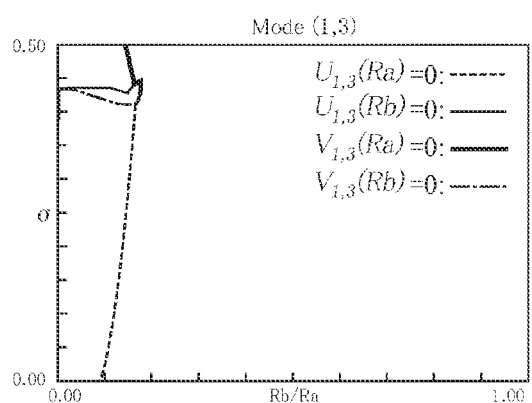
FIG. 5C is a relationship diagram in the (1, 3) mode.
Figure 5D:
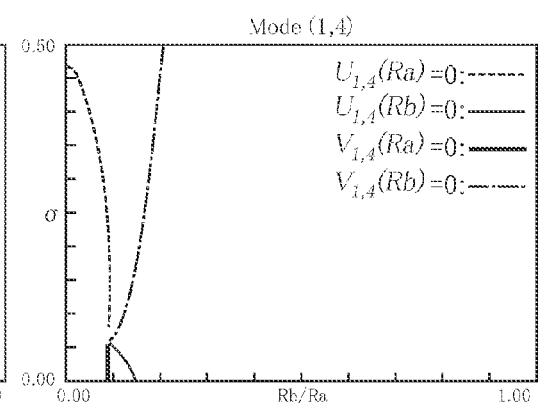
FIG. 5D is a relationship diagram in the (1, 4) mode.
Figure 6A:
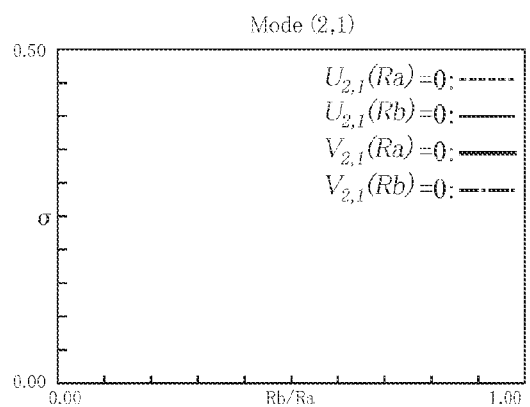
FIG. 6A is a relationship diagram in the (2, 1) mode.
Figure 6B:
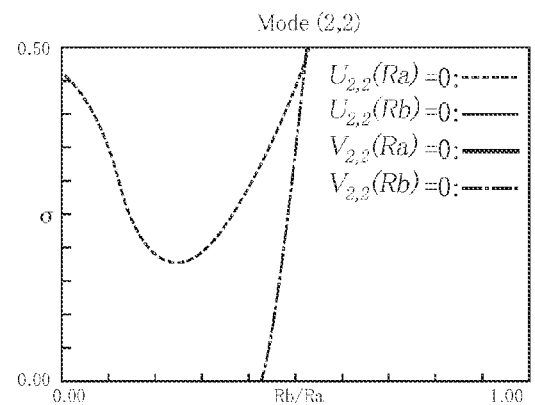
FIG. 6B is a relationship diagram in the (2, 2) mode.
Figure 6C:
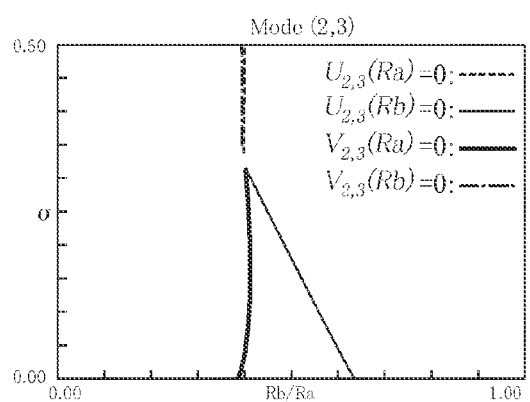
FIG. 6C is a relationship diagram in the (2, 3) mode.
Figure 6D:
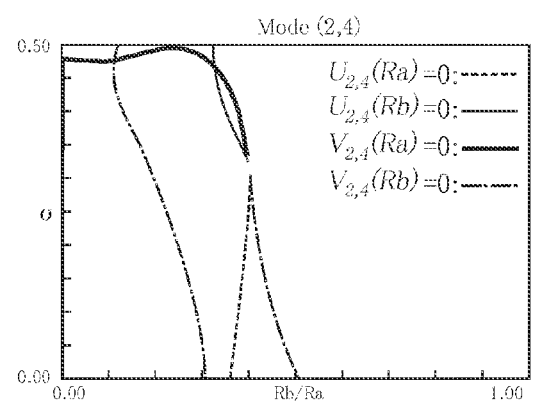
FIG. 6D is a relationship diagram in the (2, 4) mode.
Figure 7A:
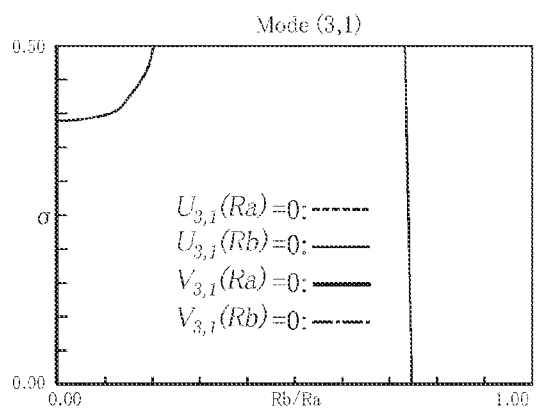
FIG. 7A is a relationship diagram in the (3, 1) mode.
Figure 7B:
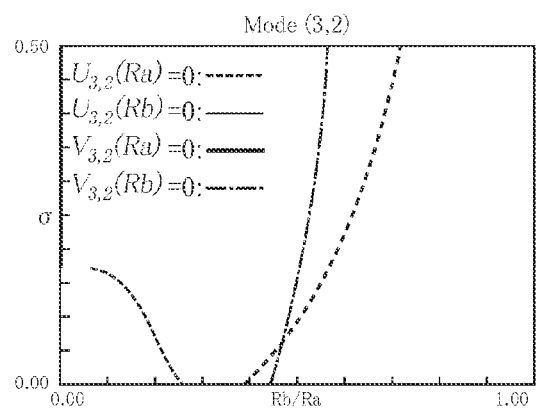
FIG. 7B is a relationship diagram in the (3, 2)
Figure 7C:
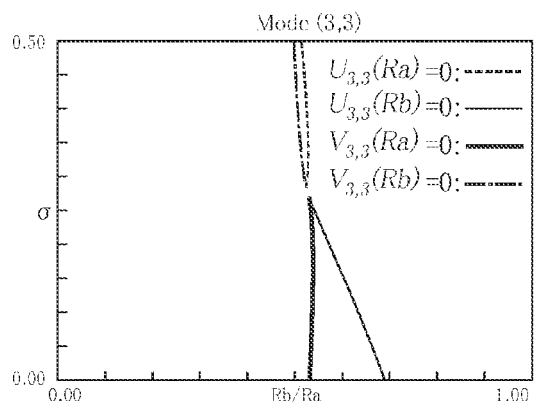
FIG. 7C is a relationship diagram in the (3, 3) mode.
Figure 7D:
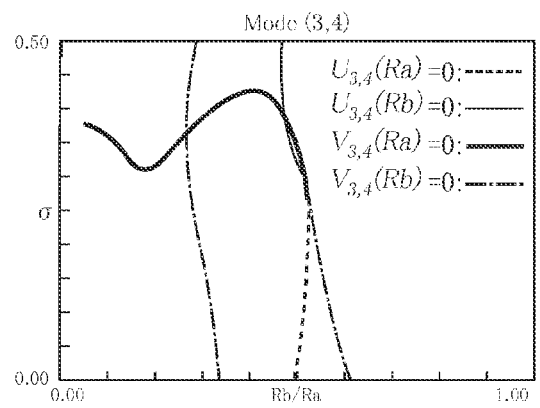
FIG. 7D is a relationship diagram in the (3,4) mode.

Referring to FIGS. 2 to 4, except the (2, 1) mode in FIG. 3A and the (3, 1) mode in FIG. 4A, any of U(Ra), U(Rb), V(Ra) and V(Rb) is observed to be 0 at appropriate Rb/Ra.

For example, in the (1,2) mode in FIG. 2B, it is indicated that V(Ra) is 0 at Rb/Ra=0.17. Thus, the resonator 20 used in the (1,2) mode is designed using a material (for example, single crystal Si) with a Poisson's ratio of 0.28 so that the ratio between the inner diameter Rb and the outer diameter Ra is set to 0.17, and the resonator 20 is held at the inner diameter portion at an angle of cos θ=0, that is, a position of θ=±π/2, thereby allowing the resonator 20 to be held without any influence on the resonant vibration of the resonator 20.

Specifically, when the outer diameter Ra is 100 μm and the diameter of the opening 21 is 17 μm to be Rb/Ra=0.17 for the resonator 20 used in the (1,2) mode, vibration in the tangential direction in the outer diameter portion of the resonator 20 can be 0. At this time, the resonator 20 is supported at the outer diameter portion of the opening 21 at the angle of cos θ=0, that is, the position of θ=±π/2, thereby achieving a holding method of the resonator 20 without any influence on the resonant vibration.

For a general material, for example, a material with a Poisson's ratio of σ=0 to 0.5, it is significantly important to check at which Rb/Ra U(Ra), U(Rb), V(Ra) and V(Rb) become 0. Thus, combinations of Rb/Ra and the Poisson's ratio σ that satisfy the following Expression (12) were checked from Expression (11) for each of the modes (n=1 to 3, m=1 to 4).

[Expression 12]

$$U(Ra) = \left| \begin{array}{c} \frac{\partial}{\partial r} J_n(hr) + A_6 \frac{n}{r} J_n(kr) + \\ A_7 \frac{\partial}{\partial r} Y_n(hr) + A_8 \frac{n}{r} Y_n(kr) \end{array} \right|_{r=Ra} = 0 \quad (12)$$

$$U(Rb) = \left| \begin{array}{c} \frac{\partial}{\partial r} J_n(hr) + A_6 \frac{n}{r} J_n(kr) + \\ A_7 \frac{\partial}{\partial r} Y_n(hr) + A_8 \frac{n}{r} Y_n(kr) \end{array} \right|_{r=Rb} = 0$$

$$V(Ra) = \left| \begin{array}{c} \frac{n}{r} J_n(hr) + A_6 \frac{\partial}{\partial r} J_n(kr) + \\ A_7 \frac{n}{r} Y_n(hr) + A_8 \frac{\partial}{\partial r} Y_n(kr) \end{array} \right|_{r=Ra} = 0$$

$$V(Rb) = \left| \begin{array}{c} \frac{n}{r} J_n(hr) + A_6 \frac{\partial}{\partial r} J_n(kr) + \\ A_7 \frac{n}{r} Y_n(hr) + A_8 \frac{\partial}{\partial r} Y_n(kr) \end{array} \right|_{r=Rb} = 0$$

The results are shown in FIGS. 5 to 7.

All materials are checked by only the Poisson's ratio being variables because there is a relationship of $$k = h(2/(1-\sigma))^{1/2}$$

between h and k from Expression (6), and with h and k being variables, the two variables are related only by the Poisson's ratio σ.

FIGS. 5 to 7 show a relationship between the Poisson's ratio σ (the ordinate) that satisfies Expression (12) and the ratio Rb/Ra (the abscissa) between the inner diameter Rb and the outer diameter Ra of the resonator 20 in each of the modes of n=1 to 3 and m=1 to 4. Specifically, if the Poisson's ratio of the resonator material is found, the vibration mode, the position where the resonator 20 is held, and the ratio between the inner diameter Rb and the outer diameter Ra of the resonator 20 can be determined from the relationship in FIGS. 5 to 7. The resonance frequency is determined by changing, for example, the size, that is, the outer diameter Ra of the resonator 20.

As such, the relationship in FIGS. 5 to 7 is previously found, thereby achieving the disk-shaped resonator 20 having high performance without loss of vibration energy through the holding portion.

The support member 22 preferably has a length $L_R$ expressed by the following Expression (13) for the resonator 20 used with vibration in the tangential direction. When a driving method using a piezoelectric effect is used by the drive source 30, the resonator 20 is used with vibration in the tangential direction, and in this case, the support member 22 preferably has the length $L_R$ expressed by Expression (13).

[Expression 13]

$$L_R = \frac{n_m \pi}{2\omega} \sqrt{\frac{E}{\rho}}, \, n_m = 1, 3, 5 \ldots \quad (13)$$

For the resonator 20 with vibration in the radial direction, the support member 22 preferably has a length $L_S$ expressed by the following Expression (14).

[Expression 14]

$$L_S = \frac{n_m \pi}{2\omega} \sqrt{\frac{KE}{\rho(2+2\sigma)}}, \, n_m = 1, 3, 5 \ldots \quad (14)$$

where $$K = \frac{10(1+\sigma)}{12+11\sigma}$$

As such, the ratio Rb/Ra between the inner diameter Rb and the outer diameter Ra of the resonator 20 is appropriately selected, and thus there may be a fixed point where the r component of the displacement in the radial direction, that is, U(Ra) or U(Rb) and the r component of the displacement in the tangential direction, that is, V(Ra) or V(Rb) are 0 on the outer diameter portion or the inner diameter portion of the resonator 20. Such a phenomenon specific to the disk-shaped resonator 20 having the opening 21 is used to hold the resonator 20 at the fixed point, thereby allowing the resonator 20 to be held without any influence on the resonant vibration of the resonator 20. This can provide the resonator 20 having extremely high quality.

A vibration amplitude and a direction thereof near the fixed point were checked.

Figure 8:
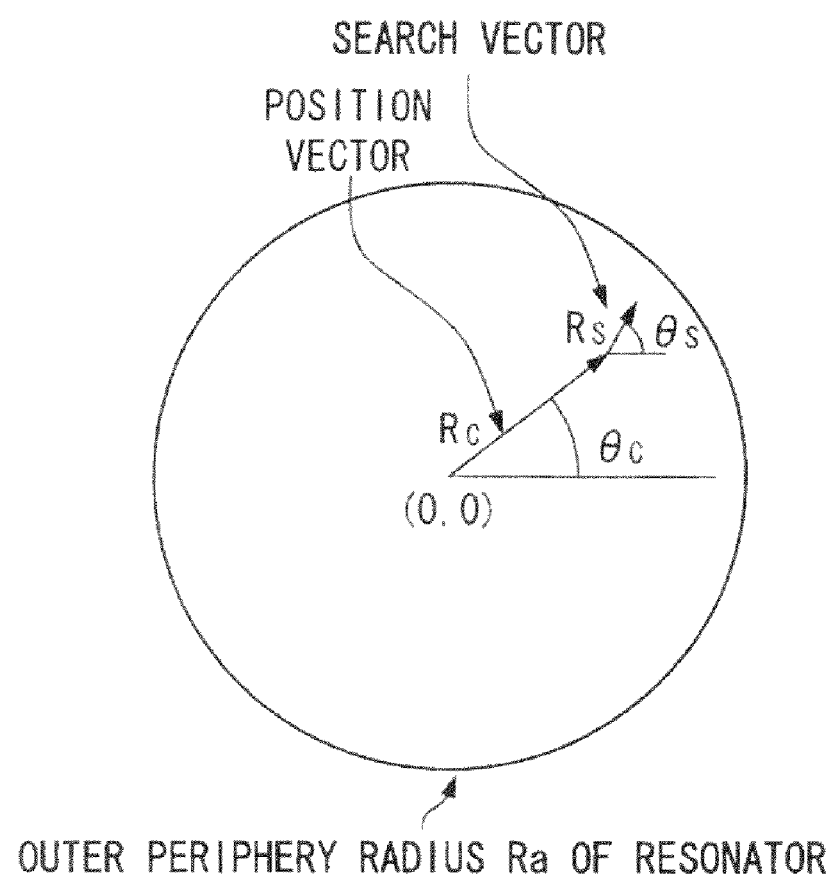
FIG. 8 shows a coordinate system when all amplitudes Ad and a vibration direction θd are calculated at a position ($r_{cs}$, $θ_{cs}$)

As shown in FIG. 8, a coordinate (Rc, θc) at the center for checking the state of vibration is determined. A vector from the center of the resonator 20 to the coordinate (Rc, θc) is referred to as a position vector. A vector indicating a position at a length Rs and an angle θs from the coordinate (Rc, θc) is referred to as a search vector, and the vibration amplitude and the direction of the resonator at a position $(r_{cs}, \theta_{cs})=(Rc+Rs, \theta c+\theta s)$ were calculated by Expression (1).

Relationships between the coordinate $(r_{cs}, \theta_{cs})$ of the position shown in FIG. 8 and the position vector and the search vector are as expressed by Expression (15).

[Expression 15]

$$r_{cs} = \sqrt{[R_c\cos(\theta_c) + R_s\cos(\theta_s)]^2 + [R_c\sin(\theta_c) + R_s\sin(\theta_s)]^2}$$
$$\theta_{cs} = \tan^{-1}[R_c\sin(\theta_c) + R_s\sin(\theta_s)]/[R_c\cos(\theta_c) + R_s\cos(\theta_s)]$$
(15)

A relationship between $U_r(r_{cs}, \theta_{cs})$ and $U_\theta(r_{cs}, \theta_{cs})$ calculated by assigning $(r_{cs}, \theta_{cs})$ calculated by Expression (15) to Expression (1) and the vibration amplitude Ad and the vibration direction θd are expressed by Expression (16).

[Expression 16]

$$A_d = \sqrt{U_r(r_{CS}, \theta_{CS})^2 + U_\theta(r_{CS}, \theta_{CS})^2}$$

$$\theta_d = \tan^{-1}[U_\theta(r_{CS}, \theta_{CS})/U_r(r_{CS}, \theta_{CS})] + \theta_c \quad (16)$$

An example of calculating the vibration amplitude Ad and the vibration direction θd will be reviewed for the following five modes. FIG. 9 shows an analysis result showing distribution of the vibration amplitude of the resonator 20 under each condition, FIG. 9A shows a case in the vibration mode (1, 2) with Rb/Ra=0.17, FIG. 9B shows a case in the vibration mode (1, 2) with Rb/Ra=0.31, FIG. 9C shows a case in the vibration mode (2, 3) with Rb/Ra=0.41, FIG. 9D shows a case in the vibration mode (2, 3) with Rb/Ra=0.43, and FIG. 9E shows a case in the vibration mode (3, 1) with Rb/Ra=0.73. The vibration amplitude is indicated in 10 levels with a region with the largest amplitude shown in white and a region with the lowest vibration in black.

Figure 10A:
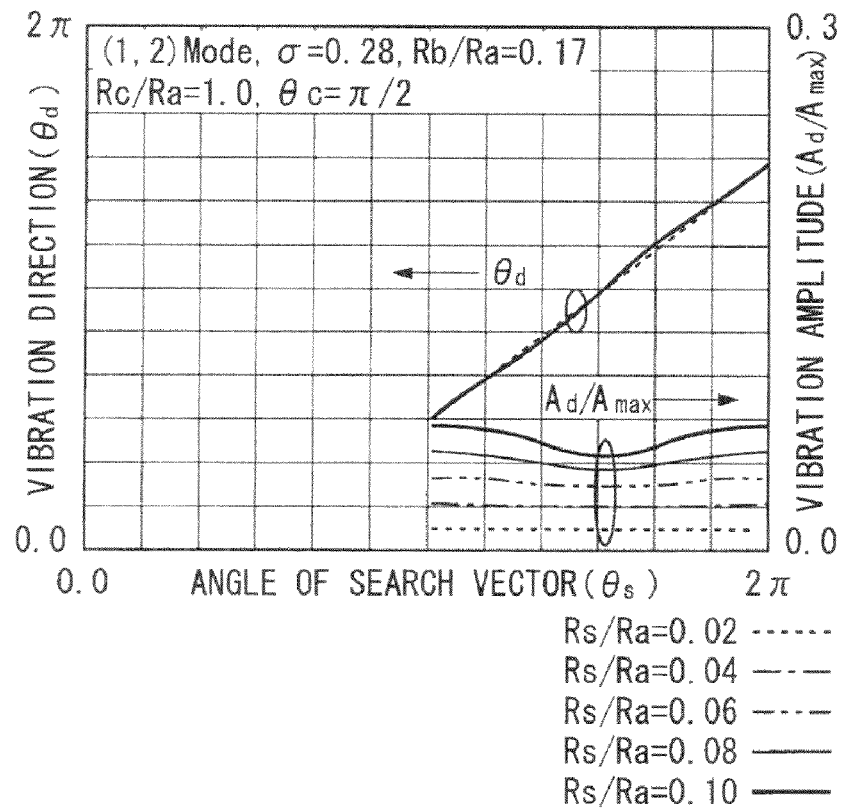
FIG. 10A shows a relationship between a vibration direction and a vibration amplitude near a fixed point of a resonator in the (1, 2) mode with Rb/Ra=0.17.

For the example in FIG. 9, a coordinate provided by the position vector is located at the position of the fixed point and the search vector is rotated around the fixed point, a vibration amplitude Ad and a vibration direction θd are calculated at the position, and the results thereof are indicated below. FIG. 10A shows the amplitude direction θd and a value Ad/Amax obtained by standardizing all vibration amplitudes with a maximum vibration amplitude using five search vectors having lengths of 2%, 4%, 6%, 8% and 10% of the outer diameter radius of the resonator 20 with changing angles θs of the search vector for the case in the (1, 2) mode with Rb/Ra=0.17 in FIG. 9A.

The fixed point in the (1, 2) mode with Rb/Ra=0.17 is located at two spots at an angle θb=π/2 and 3π/2 on the outer periphery of the resonator 20 as shown in FIG. 9A. FIG. 10A shows the vibration amplitude and the vibration direction calculated around the fixed point located at the angle θs=π/2. This state is schematically shown as a vibration vector as in FIG. 10B.

Figure 10B:
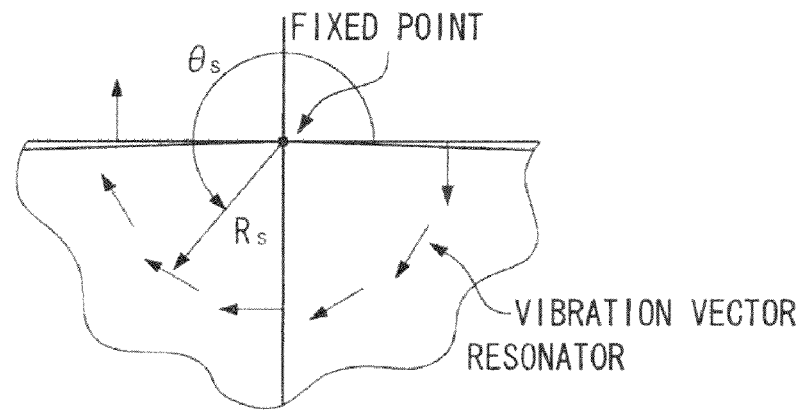
FIG. 10B is a schematic diagram of a vibration vector near the fixed point.

Specifically, it can be seen from FIG. 10A that the vibration amplitude (Ad/Amax) becomes smaller in positions closer to the fixed point in the resonator 20, but the vibration amplitude becomes substantially constant irrespective of the angle θs of the search vector, the vibration direction (θd) substantially changes by it from π/2 to 3π/2, and the resonator 20 vibrates in the very state shown in FIG. 10B. Specifically, in this case, it can be seen that substantially circular motion is performed around the fixed point near the fixed point.

Figure 11A:
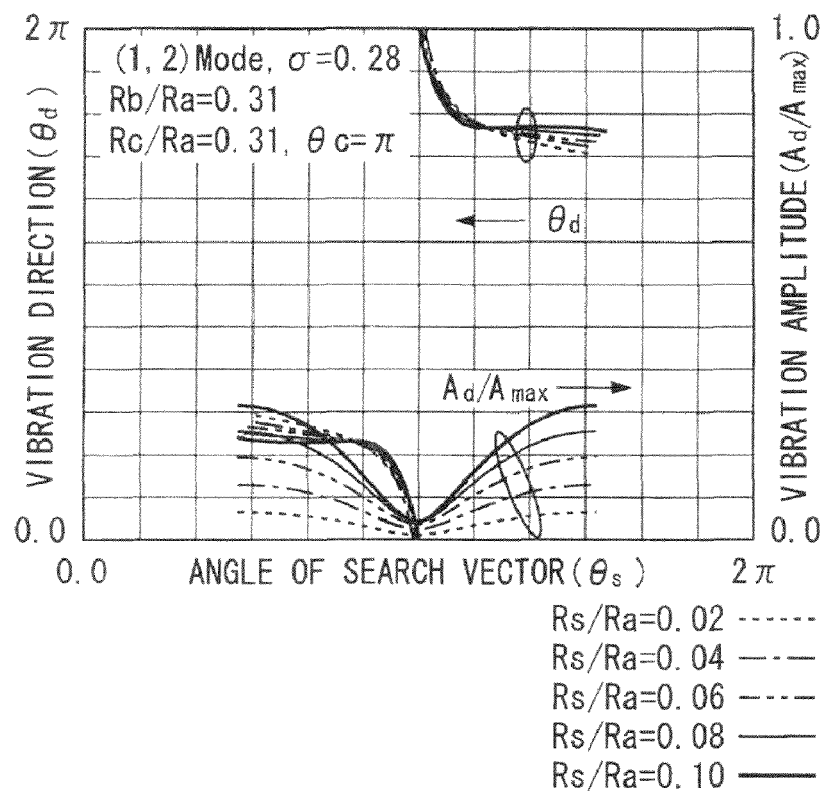
FIG. 11A shows a relationship between a vibration direction and a vibration amplitude near a fixed point of a resonator in the (1, 2) mode with Rb/Ra=0.31.

FIG. 11A shows calculation in the vibration mode (1, 2) with Rb/Ra=0.31 shown in FIG. 9B.

Figure 11B:
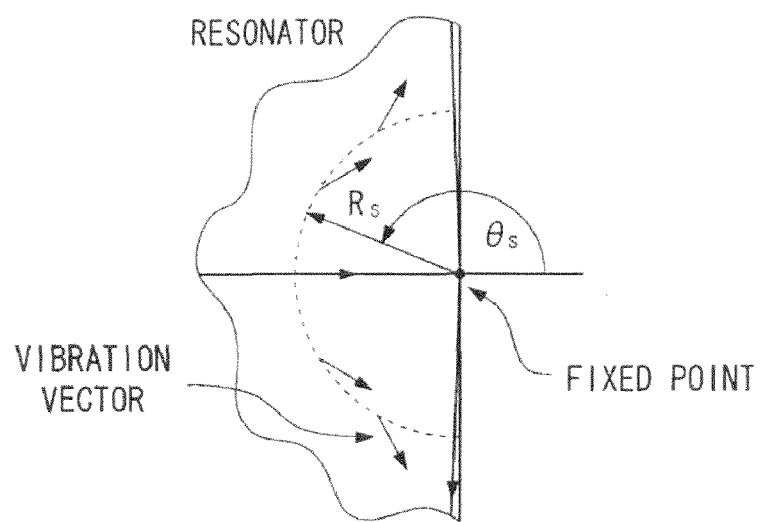
FIG. 11B is a schematic diagram of a vibration vector near the fixed point.

This example shows a case where a fixed point is formed on the inner diameter of the resonator 20, and a vibration state near the fixed point is checked using five search vectors having lengths of 2%, 4%, 6%, 8% and 10% of the outer diameter radius of the resonator 20 around the fixed point at the position it on the inner diameter for a calculation position. The vibration direction is also π/2 at an angle of the search vector θs=π/2, the vibration direction is 0 at an angle of the search vector θs=π, the vibration direction is also 3π/2 at an angle of the search vector θs=3π/2. This state is shown in FIG. 11B with the same concept as FIG. 10B above.

Specifically, in the resonator 20, two points on the inner periphery with the fixed point therebetween oscillate in the opposite directions, and an intermediate position contracts when the two points pull each other (the two points are displaced in directions away from each other) according to the concept of the Poisson's ratio, and expands when the two points push each other (the two points are displaced in directions approaching each other).

Figure 12:
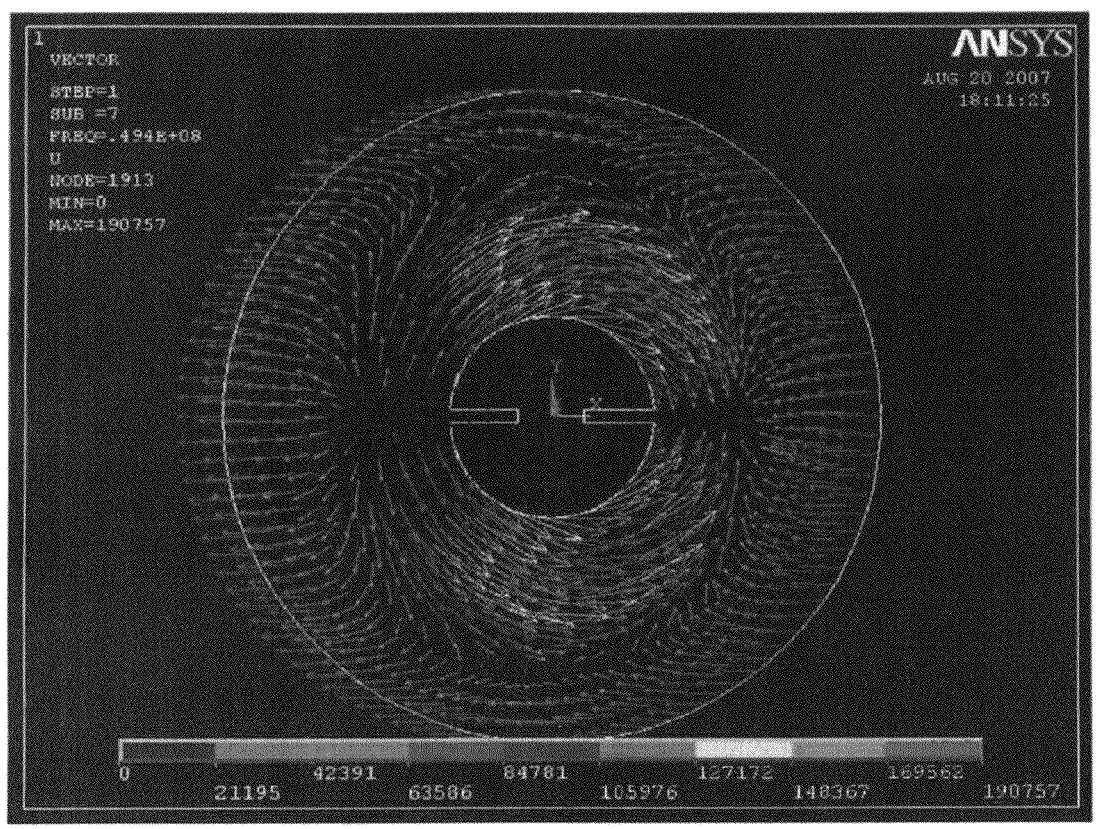
FIG. 12 shows a result of simulating the vibration vector for the example in FIG. 11.

FIG. 12 shows a result of simulating the vibration vector with ANSYS by a finite element method for the resonator 20 in the (1, 2) mode with Rb/Ra=0.31 shown in FIG. 11A. FIG. 12 shows a state where when opposite sides of the fixed point pull each other, a position perpendicular thereto contracts, and when the opposite sides push each other, the position perpendicular thereto expands as in FIG. 11B.

Figure 13A:
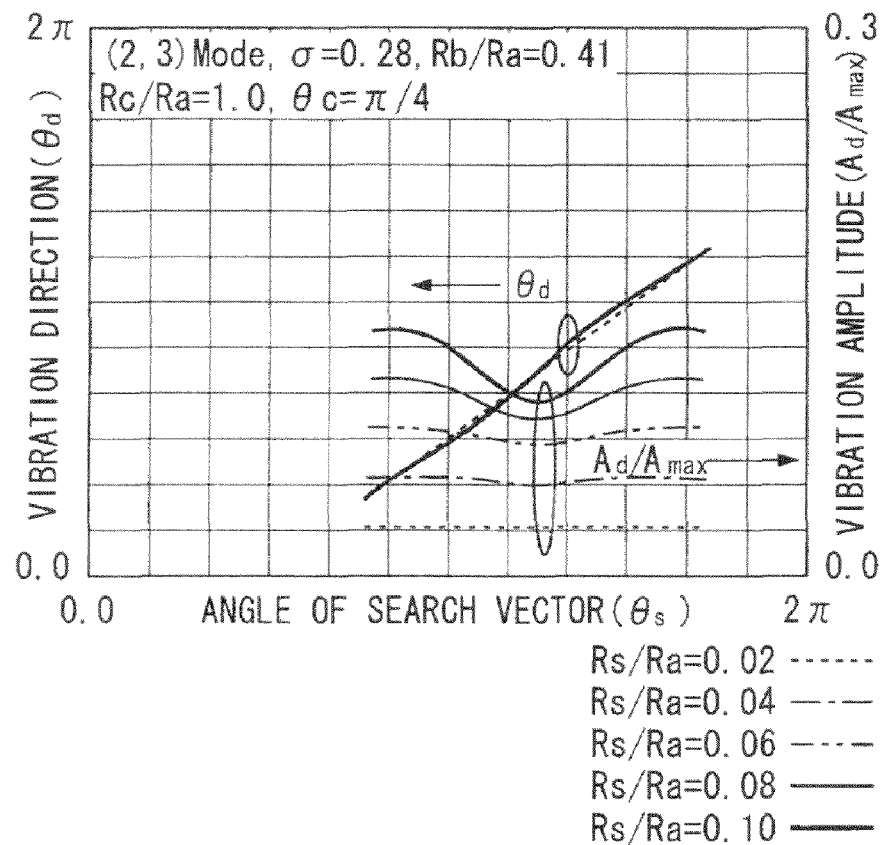
FIG. 13A shows a relationship between a vibration direction and a vibration amplitude near a fixed point of a resonator in the (2, 3) mode with Rb/Ra=0.41.

FIG. 13A shows a case of checking the resonator 20 in the vibration mode (2, 3) with Rb/Ra=0.41 shown in FIG. 9C. In the resonator 20, fixed points are located at positions of π/4, 3π/4, 5π/4 and 7π/4 on the outer diameter portion of the resonator 20.

The fixed points of the resonator 20 in the (2, 3) mode with Rb/Ra=0.41 are located at four spots of π/4, 3π/4, 5π/4 and 7π/4 on the outer diameter portion of the resonator 20 as shown in FIG. 9C. FIG. 13A shows calculation of a vibration amplitude and a vibration direction near the fixed point at the position of π/4. The vibration direction is π/4 at an angle of the search vector 3π/4, the vibration direction is 3π/4 at an angle of the search vector θs=5π/4, and the vibration direction is 5π/4 at an angle of the search vector θs=7π/4. This state is schematically shown as in FIG. 13B as a vibration vector with the same concept as in FIGS. 10B and 11B above. This is basically completely the same vibration as in FIG. 10B, and it is found that the amplitude of the vibration vector also becomes constant at a position closer to the fixed point, and ideal rotary motion is performed in the position.

Figure 13B:
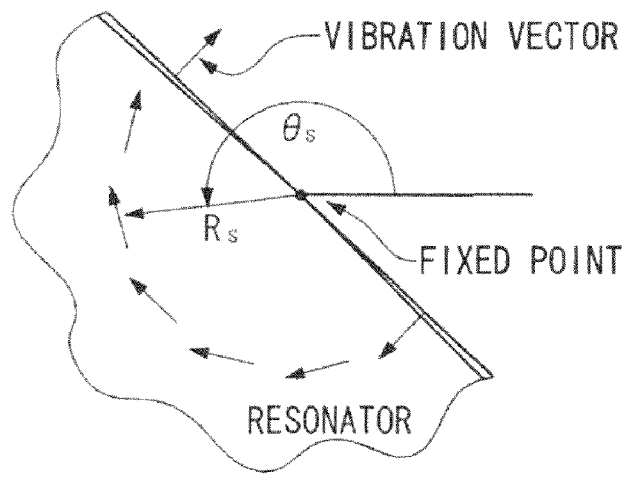
FIG. 13B is a schematic diagram of a vibration vector near the fixed point.
Figure 14:
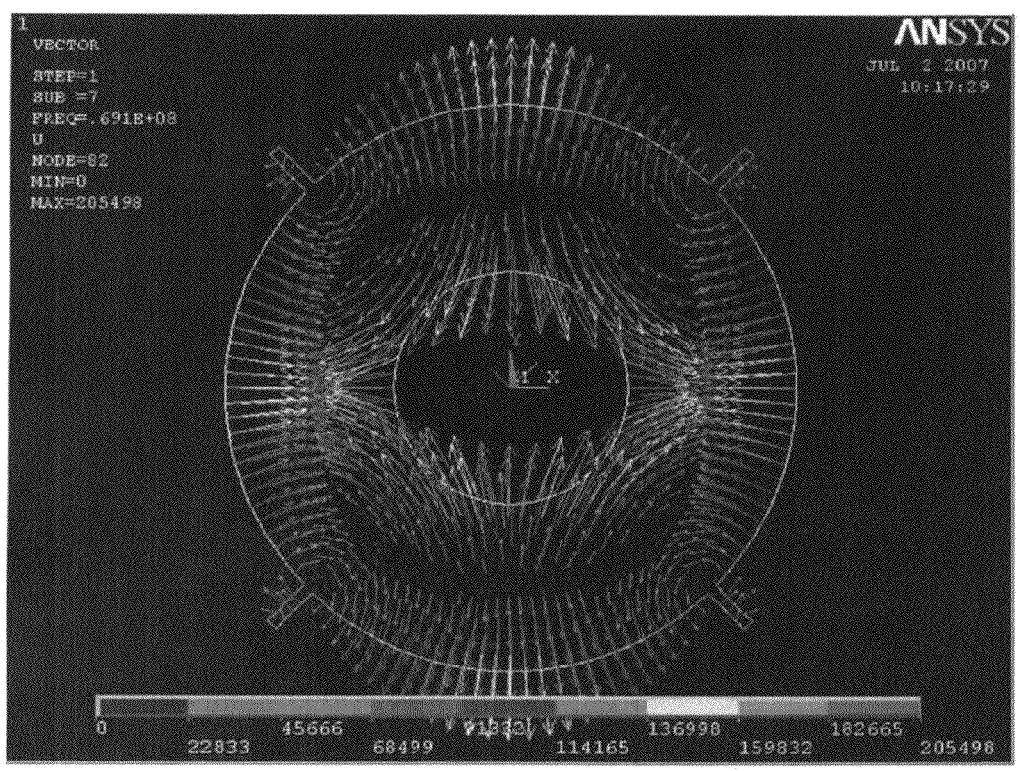
FIG. 14 shows a result of simulating the vibration vector for the example in FIG. 13.

FIG. 14 shows a result of simulating the vibration vector with ANSYS for the (2, 3) mode with Rb/Ra=0.41 shown in FIG. 13A. The rotary motion as in FIG. 13B is shown around and near fixed points at four spots (π/4, 3π/4, 5π/4 and 7π/4) on the outer diameter.

Figure 15:
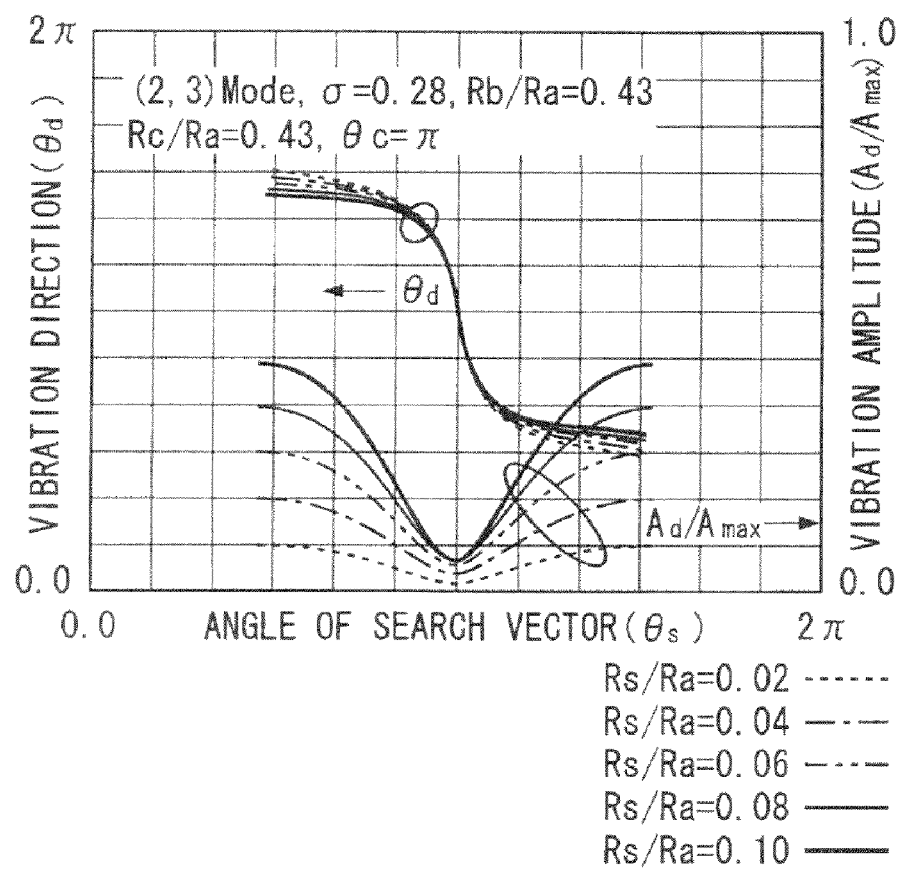
FIG. 15 shows a relationship between a vibration direction and a vibration amplitude near a fixed point of a resonator in the (2, 3) mode with Rb/Ra=0.43.

FIG. 15 shows an example of the resonator 20 in FIG. 9D in the vibration mode (2, 3) with Rb/Ra=0.43, and fixed points are located at positions of 0, π/2, it and 3π/2 on the inner diameter.

This example shows a case where the fixed point is formed on the inner diameter of the resonator 20, and a vibration state near the fixed point is checked using five search vectors having lengths of 2%, 4%, 6%, 8% and 10% of the outer diameter radius of the resonator 20 around the fixed point at the position it on the inner diameter for a calculation position. The vibration direction is 3π/2 at an angle of the search vector θs=π/2, the vibration direction is π at an angle of the search vector θs=π, and the vibration direction is also π/2 at an angle of the search vector θs=3π/2. In this state, the direction of the vibration vector differs by π, but the state is basically completely the same as in FIG. 11B.

Figure 16:
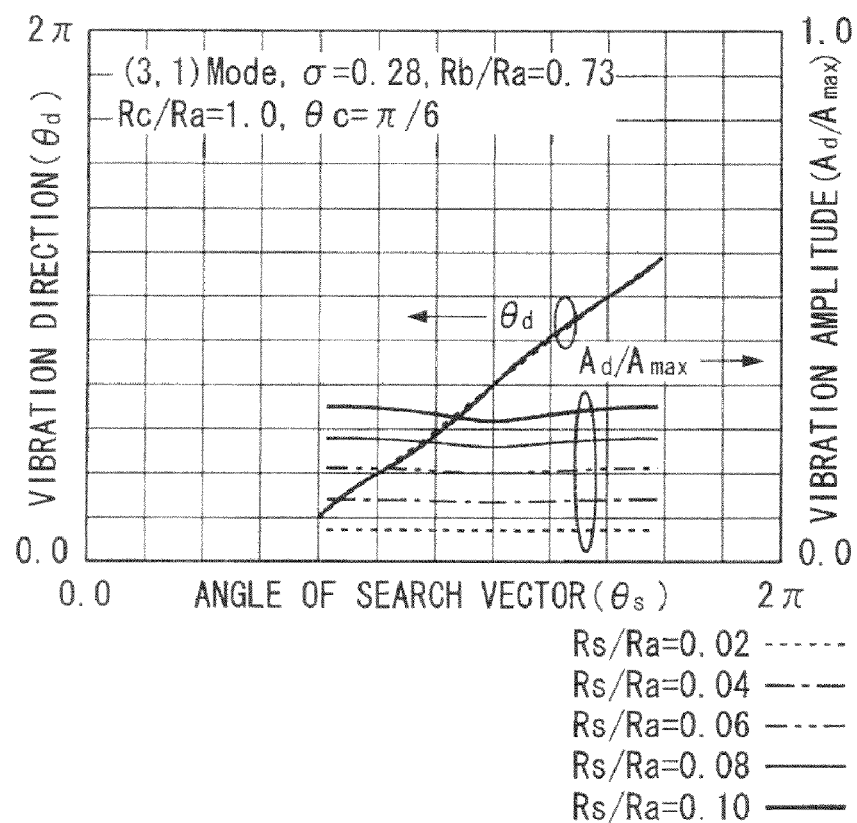
FIG. 16 shows a relationship between a vibration direction and a vibration amplitude near a fixed point of a resonator in the (3, 1) mode with Rb/Ra=0.73.

FIG. 16 shows an example of the resonator 20 in the vibration mode (3, 1) with Rb/Ra=0.73 in FIG. 9E. Fixed points are located in 6 spots of π/6, π/2, 5π/6, 7π/6, 3π/2 and 11π/6 on the outer diameter portion of the resonator 20.

In this example, a vibration state near the fixed point is checked using five search vectors having lengths of 2%, 4%, 6%, 8% and 10% of the outer diameter radius, around the fixed point at π/6 on the outer diameter as a position for calculation of the vibration state among the six fixed points formed on the outer diameter.

The vibration direction is π/6 at an angle of the search vector θs=2π/3, the vibration direction is 2π/3 at an angle of the search vector θs=7π/6, and the vibration direction is 7π/6 at an angle of the search vector θs=5π/3. In this state, the direction of the vibration vector differs by π/3, but the state is basically completely the same as in FIG. 10B, and pure rotary motion can be observed also in this case.

For the five vibration modes of the plane mechanical resonator 20 having the opening, the states of vibration near the fixed point formed on the outer periphery or the inner periphery have been checked. The results showed that basically two types of vibrations occur near the fixed point. This will be newly shown as in FIG. 17.

Figure 17A:
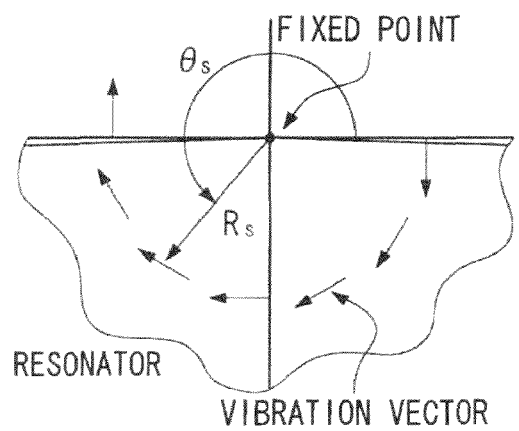
FIG. 17 shows four examples of states of vibrations that occur in the resonator near the fixed point.

In FIG. 17A, the vibration amplitude in the tangential direction becomes 0 on the outer periphery or the inner periphery of the resonator 20 when $V_r(r)|_{r=Ra\ or\ Rb} \neq 0$ and $V_\theta(r)|_{r=Ra\ or\ Rb}=0$ in an expression expressing displacement, that is, vibration of the resonator 20 expressed in Expression (1). At this time, the vibration amplitude in the radial direction is obtained by multiplying Vr(r) by cos(nθ) as expressed in Expression (1), and thus when cos(nθ)=0, the vibration amplitude in the radial direction also becomes 0, and the fixed point is formed at this position.

With slight displacement from the fixed point as r=Ra−∈ (∈<<Ra), a tangential component appears, and the direction thereof may be opposite from that in FIG. 17A. This is shown as in FIG. 17C.

Figure 17B:
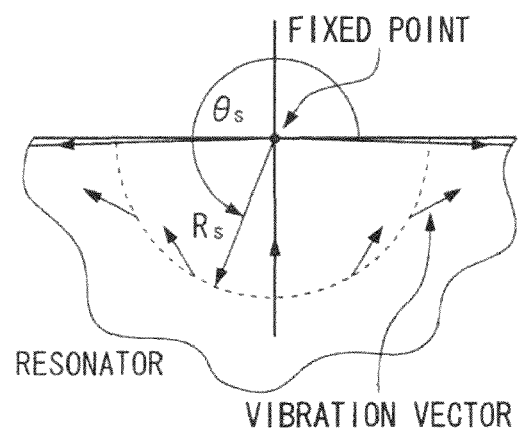
Figure 17C:
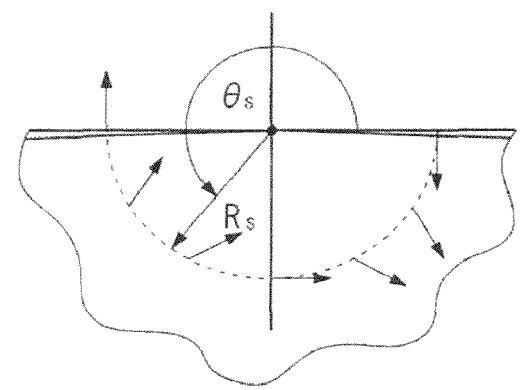
Figure 17D:
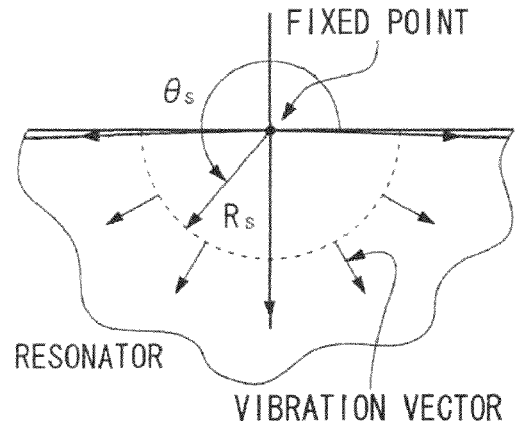

Similarly to this, in the case where the vibration direction in the radial direction is opposite from that in FIG. 17B when $V_\theta(r)|_{r=Ra\ or\ Rb} \neq 0$ and $V_r(r)|_{r=Ra\ or\ Rb}=0$, expansion on one side around the fixed point is supposed as shown in FIG. 17D.

As such, four vibration modes are supposed near the fixed point, and considering only the outer periphery or the inner periphery of the resonator 20, motions can be limited to two motions: seesaw motion around the fixed point in the cases in FIGS. 17A and 17C (referred to as a case (A)), and tension (compression) motion around the fixed point in the cases in FIGS. 17B and 17D (referred to as a case (B)).

For the case (A), since the seesaw motion is performed with a minute amplitude around the fixed point as a support, and an end of the holding member 22 connected to this place performs seesaw motion, and the other end is secured. The seesaw motion corresponds to "pinned" for a point and "simply supported" for a line for a general boundary condition.

Figure 18:
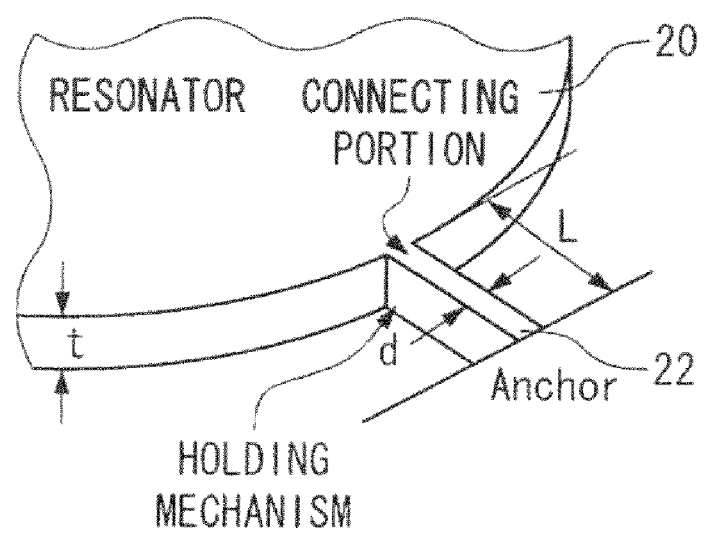
FIG. 18 shows a holding member of the resonator.

Specifically, for designing the holding member 22 as a "rod or comparable structure", a single-span beam with a boundary condition of pinned-clamped applies thereto, and for designing the holding member 22 as a "plate or comparable structure", the holding member 22 is designed with a boundary condition of simply supported-free-clamped-free. Outlines of these structures are shown in FIG. 18.

When the holding member 22 is supposed to be the single-span beam, the resonance frequency f thereof is as expressed by the following expression:

[Expression 17]

$$f_i = \frac{\lambda_i^2}{2\pi L^2}\sqrt{\frac{EI}{m}} = \frac{\lambda_i^2}{4\pi\sqrt{3}\,L^2}d\sqrt{\frac{E}{\rho}} \tag{17}$$

where i: harmonic order, L: length of beam, E: Young's modulus, I: area moment, m: mass per unit length, ρ: density, d: thickness of beam. $\lambda_i$ can be provided by the following Expression (18).

[Expression 18]

$$\tan \lambda_i = \tan h \lambda_i \tag{18}$$

Similarly, for the plate structure, the vibration frequency can be calculated using basically the same concept.

As such, the frequency and the resonance frequency of the resonator 20 are designed to be equal, thereby allowing free vibration without interference, and significantly reducing transfer of the vibration energy in a stationary state.

In the case (B), tension and compression motion occurs around the fixed point. In this case, it is realistic that the holding structure has as narrow a connection width d as possible between the resonator 20 and the holding member 22, but an actual width d is determined by a trade-off between 1) a limit of production accuracy, 2) a production yield, 3) mechanical strength for mechanically holding the resonator 20, or the like.

According to the above-described sensor 10, the resonator 20 is supported on the anchor by the holding member 22 constituted by the single-span beam set so that the boundary condition on the side of the resonator 20 is pinned and the boundary condition on the side of the anchor that supports the resonator 20 is clamped at the fixed point without vibrations of the radial component and the tangential component, and this can prevent vibration energy of the resonator 20 from being lost through the holding member 22, and avoid a state to disturb the vibration mode. Therefore, a sensor 10 having high sensitivity can be achieved.

As such, the sensor 10 can detect an object having a mass or the mass with high sensitivity. Also, the resonator 20 can be produced by a MEMS technique using so-called Si single crystal as a structure material, and thus the sensor 10 can be integrated into the same chip as an Si semiconductor. In this case, a detection device of a minute substance can be provided that is extremely inexpensive and has high performance.

The example of the resonator 20 made of Si single crystal (Poisson's ratio σ=0.28) has been described above, but it should be understood that the same review can be performed to obtain the same advantage for different materials.

Further, the configurations described in the embodiment may be chosen or changed to other configurations without departing from the gist of the present invention.

The invention claimed is:
1. A detection sensor comprising:
a disk-shaped resonator having a vibration characteristic changed by adherence or adsorption of a substance having a mass;
a driving unit that causes vibration of the resonator; and
a detection unit that detects a change in vibration of the resonator to detect the substance, wherein the resonator having a ring shape with an outer diameter Ra and an inner diameter Rb with an opening formed at the center;

the resonator being formed of the outer diameter Ra and the inner diameter Rb that substantially satisfy $U(r)=0$ or $V(r)=0$ when $r=Ra$ or $Rb$ for displacement $U(r)$ in a radial displacement and displacement $V(r)$ in a tangential direction expressed by Expression (19) in a position $r$ on a position coordinate $(r, \theta)$ when the resonator vibrates; and the resonator is supported on an anchor by a single-span beam set so that a boundary condition on a side of the resonator is pinned and a boundary condition on a side of the anchor that supports the resonator is clamped, where Expression 19 is expressed as:

$$U(r) = \frac{\partial}{\partial r}J_n(hr) + A_6 \frac{n}{r}J_n(kr) + A_7 \frac{\partial}{\partial r}Y_n(hr) + A_8 \frac{n}{r}Y_n(kr) \quad (19)$$
$$V(r) = \frac{n}{r}J_n(hr) + A_6 \frac{\partial}{\partial r}J_n(kr) + A_7 \frac{n}{r}Y_n(hr) + A_8 \frac{\partial}{\partial r}Y_n(kr)$$

where $$h = \omega\sqrt{\frac{\rho(1-\sigma^2)}{E}}, \ k = \omega\sqrt{\frac{\rho(2+2\sigma)}{E}}, \ k = h\sqrt{\frac{2}{1-\sigma}}, \ \text{and}$$

where $\sigma$ represents Poisson's ratio of a resonator material, E represents Young's modulus of the resonator material, $\rho$ represents a density of the resonator material, $\omega$ represents angular frequency, n represents a degree of vibration mode, and $A_6$, $A_7$ and $A_8$ are constants uniquely determined by natural vibration mode specified by outer diameter and inner diameter of resonator, Young's modulus, density and Poisson's ratio of resonator material, and the boundary condition (in this case, free-free condition) of the resonator, wherein the single-span beam has a length and a width set so that a vibration frequency thereof is substantially equal to a vibration frequency of the resonator.

2. The detection sensor according to claim 1, wherein in a case where $U(r)=0$ or $V(r)=0$ is substantially satisfied when $r=Ra$ in the Expression (19), the resonator is supported at an outer diameter portion.

3. The detection sensor according to claim 2, wherein in a case where $U(r)=0$ is substantially satisfied when $r=Ra$ in the Expression (19), the resonator is supported at a position $\theta$ where $\sin(n\theta)=0$.

4. The detection sensor according to claim 2, wherein in a case where $V(r)=0$ is substantially satisfied when $r=Ra$ in the Expression (19), the resonator is supported at a position $\theta$ where $\cos(n\theta)=0$.

5. The detection sensor according to claim 1, wherein the detection unit detects an amount of the substance adhering to the resonator.

6. The detection sensor according to claim 1, wherein the substance is a particular molecule, or multiple types of molecules having a particular property or characteristic.

* * * * *

UNITED STATES PATENT AND TRADEMARK OFFICE
CERTIFICATE OF CORRECTION

PATENT NO.        : 8,196,451 B2                                    Page 1 of 1
APPLICATION NO.   : 12/661194
DATED             : June 12, 2012
INVENTOR(S)       : Mitsuo Konno It is certified that error appears in the above-identified patent and that said Letters Patent is hereby corrected as shown below:

Column 13 line 56, delete "$\theta b = n/2$" and insert therefor -- $\theta b = \pi/2$ --

Column 13 line 67, delete "it" and insert therefor -- $\pi$ --

Column 14 line 11, delete "it" and insert therefor -- $\pi$ --

Column 14 line 12, delete "n/2" and insert therefor -- $\pi/2$ --

Column 14 line 14, delete "$\theta s = n$" and insert therefor -- $\theta s = \pi$ --

Column 14 line 42, delete "n/4" and insert therefor -- $\pi/4$ --

Column 14 line 59, delete "it" and insert therefor -- $\pi$ --

Column 14 line 66, delete "it" and insert therefor -- $\pi$ --

Signed and Sealed this
Thirteenth Day of November, 2012

David J. Kappos
*Director of the United States Patent and Trademark Office*